US007217276B2

(12) United States Patent
Henderson et al.

(10) Patent No.: US 7,217,276 B2
(45) Date of Patent: May 15, 2007

(54) INSTRUMENT GUIDANCE METHOD AND SYSTEM FOR IMAGE GUIDED SURGERY

(75) Inventors: Jaimie Henderson, St. Louis, MO (US); Richard D Bucholz, St. Louis, MO (US); Kurt R Smith, Eldorado Springs, CO (US); Kevin J Frank, Lafayette, CO (US); John B Clayton, Superior, CO (US); Catalina J Carroll, Memphis, TN (US); Phillip T Ulberg, Reno, NV (US)

(73) Assignee: Surgical Navigational Technologies, Inc., Louisville, CO (US)

( * ) Notice: Subject to any disclaimer, the term of this patent is extended or adjusted under 35 U.S.C. 154(b) by 724 days.

(21) Appl. No.: 10/271,353

(22) Filed: Oct. 15, 2002

(65) Prior Publication Data

US 2003/0114752 A1 Jun. 19, 2003

Related U.S. Application Data

(63) Continuation of application No. 09/557,004, filed on Apr. 20, 2000, now Pat. No. 6,491,699.

(60) Provisional application No. 60/130,118, filed on Apr. 20, 1999.

(51) Int. Cl.
*A61B 19/00* (2006.01)

(52) U.S. Cl. ........................................ 606/130; 600/429

(58) Field of Classification Search ................ 606/130; 600/429; 604/130, 116, 117

See application file for complete search history.

(56) References Cited

U.S. PATENT DOCUMENTS 1,576,781 A 3/1926 Phillips (Continued)

FOREIGN PATENT DOCUMENTS

CA 964149 3/1975

(Continued)

OTHER PUBLICATIONS

Hahn, et al., "Needle Biopsy of Intracranial Lesions Guided by Computerized Tomography," Neurosurgery, Jul. 1979, 11-15, vol. 5, Part 1.

(Continued)

*Primary Examiner*—Nicholas D. Lucchesi
*Assistant Examiner*—Melissa A. McCorkle
(74) *Attorney, Agent, or Firm*—Harness, Dickey & Pierce, P.L.C.

(57) ABSTRACT

Generally, the present invention is directed to a method and system for a aligning surgical guide instrument over a burr hole in a patient's body. More particularly, the present invention is directed to a stand-alone instrument guidance unit that is attachable to a patient's skull. Adjustments of a surgical instrument can be made in x, y, z, and angular directions using the system and method of the present invention. In one aspect of the present invention, an instrument guide unit includes an instrument guide for guiding a surgical instrument into the body of a patient and a base unit operative to be secured to the body in an area in which surgery is to occur. The base unit is coupled to the instrument guide. An adjustment mechanism, coupled to the base unit and the instrument guide, is operative to adjust the instrument guide in lateral directions with respect the surface of the area. The adjustment mechanism is operative to adjust the instrument guide in x and y directions. The adjustment mechanism includes an x direction control mechanism for adjusting the instrument in an x direction and a y direction control mechanism for adjusting the instrument in a y direction. The y direction control mechanism may be coupled to the x direction control mechanism. The positional movement of the surgical instrument in the z direction may be tracked by sensing the location of a transducer coupled to the surgical instrument.

32 Claims, 9 Drawing Sheets

U.S. PATENT DOCUMENTS 1,735,726 A 11/1929 Bornhardt
2,407,845 A 9/1946 Nemeyer
2,650,588 A 9/1953 Drew
2,697,433 A 12/1954 Sehnder
3,016,899 A 1/1962 Stenvall
3,017,887 A 1/1962 Heyer
3,061,936 A 11/1962 Dobbeleer
3,073,310 A 1/1963 Mocarski
3,109,588 A 11/1963 Polhemus et al.
3,294,083 A 12/1966 Alderson
3,367,326 A 2/1968 Frazier
3,439,256 A 4/1969 Kähne et al.
3,577,160 A 5/1971 White
3,614,950 A 10/1971 Rabey
3,644,825 A 2/1972 Davis, Jr. et al.
3,674,014 A 7/1972 Tillander
3,702,935 A 11/1972 Carey et al.
3,704,707 A 12/1972 Halloran
3,821,469 A 6/1974 Whetstone et al.
3,868,565 A 2/1975 Kuipers
3,941,127 A 3/1976 Froning
3,983,474 A 9/1976 Kuipers
4,017,858 A 4/1977 Kuipers
4,037,592 A 7/1977 Kronner
4,052,620 A 10/1977 Brunnett
4,054,881 A 10/1977 Raab
4,058,114 A 11/1977 Soldner
4,117,337 A 9/1978 Staats
4,173,228 A 11/1979 Van Steenwyk et al.
4,182,312 A 1/1980 Mushabac
4,202,349 A 5/1980 Jones
4,228,799 A 10/1980 Anichkov et al.
4,232,338 A 11/1980 Netravali et al.
4,256,112 A 3/1981 Kopf et al.
4,262,306 A 4/1981 Renner
4,287,809 A 9/1981 Egli et al.
4,298,874 A 11/1981 Kuipers
4,314,251 A 2/1982 Raab
4,317,078 A 2/1982 Weed et al.
4,319,136 A 3/1982 Jinkins
4,328,548 A 5/1982 Crow et al.
4,328,813 A 5/1982 Ray
4,339,953 A 7/1982 Iwasaki
4,341,220 A 7/1982 Perry
4,346,384 A 8/1982 Raab
4,358,856 A 11/1982 Stivender et al.
4,368,536 A 1/1983 Pfeiler
4,396,885 A 8/1983 Constant
4,396,945 A 8/1983 DiMatteo et al.
4,403,321 A 9/1983 DiMarco
4,418,422 A 11/1983 Richter et al.
4,419,012 A 12/1983 Stephenson et al.
4,422,041 A 12/1983 Lienau
4,431,005 A 2/1984 McCormick
4,465,069 A 8/1984 Barbier et al.
4,485,815 A 12/1984 Amplatz
4,506,676 A 3/1985 Duska
4,543,959 A 10/1985 Sepponen
4,548,208 A 10/1985 Niemi
4,571,834 A 2/1986 Fraser et al.
4,572,198 A 2/1986 Codrington
4,583,538 A 4/1986 Onik et al.
4,584,577 A 4/1986 Temple
4,602,622 A 7/1986 Bär et al.
4,608,977 A 9/1986 Brown
4,613,866 A 9/1986 Blood
4,617,925 A 10/1986 Laitinen
4,618,978 A 10/1986 Cosman
4,621,628 A 11/1986 Brudermann
4,625,718 A 12/1986 Olerud et al.
4,638,798 A 1/1987 Shelden et al.
4,642,786 A 2/1987 Hansen
4,645,343 A 2/1987 Stockdale et al.
4,649,504 A 3/1987 Krouglicof et al.
4,651,732 A 3/1987 Frederick
4,653,509 A 3/1987 Oloff et al.
4,659,971 A 4/1987 Suzuki et al.
4,660,970 A 4/1987 Ferrano
4,673,352 A 6/1987 Hansen
4,686,977 A 8/1987 Cosma
4,686,997 A 8/1987 Oloff et al.
4,688,037 A 8/1987 Krieg
4,701,049 A 10/1987 Beckmann et al.
4,705,395 A 11/1987 Hageniers
4,705,401 A 11/1987 Addleman et al.
4,706,665 A 11/1987 Gouda
4,709,156 A 11/1987 Murphy et al.
4,710,708 A 12/1987 Rorden et al.
4,719,419 A 1/1988 Dawley
4,722,056 A 1/1988 Roberts et al.
4,722,336 A 2/1988 Kim et al.
4,723,544 A 2/1988 Moore et al.
4,727,565 A 2/1988 Ericson
RE32,619 E 3/1988 Damadian
4,733,661 A 3/1988 Palestrant
4,733,969 A 3/1988 Case et al.
4,737,032 A 4/1988 Addleman et al.
4,737,794 A 4/1988 Jones
4,737,921 A 4/1988 Goldwasser et al.
4,742,356 A 5/1988 Kuipers
4,742,815 A 5/1988 Ninan et al.
4,743,770 A 5/1988 Lee
4,743,771 A 5/1988 Sacks et al.
4,745,290 A 5/1988 Frankel et al.
4,750,487 A 6/1988 Zanetti
4,753,528 A 6/1988 Hines et al.
4,761,072 A 8/1988 Pryor
4,764,016 A 8/1988 Johansson
4,771,787 A 9/1988 Wurster et al.
4,776,749 A 10/1988 Wanzenberg et al.
4,779,212 A 10/1988 Levy
4,782,239 A 11/1988 Hirose et al.
4,788,481 A 11/1988 Niwa
4,791,934 A 12/1988 Brunnett
4,793,355 A 12/1988 Crum et al.
4,794,262 A 12/1988 Sato et al.
4,797,907 A 1/1989 Anderton
4,803,976 A 2/1989 Frigg et al.
4,804,261 A 2/1989 Kirschen
4,805,615 A 2/1989 Carol
4,809,694 A 3/1989 Ferrara
4,821,200 A 4/1989 Öberg
4,821,206 A 4/1989 Arora
4,821,731 A 4/1989 Martinelli et al.
4,822,163 A 4/1989 Schmidt
4,825,091 A 4/1989 Breyer et al.
4,829,373 A 5/1989 Leberl et al.
4,836,778 A 6/1989 Baumrind et al.
4,838,265 A 6/1989 Cosman et al.
4,841,967 A 6/1989 Chang et al.
4,845,771 A 7/1989 Wislocki et al.
4,849,692 A 7/1989 Blood
4,860,331 A 8/1989 Williams et al.
4,862,893 A 9/1989 Martinelli
4,869,247 A 9/1989 Howard, III et al.
4,875,165 A 10/1989 Fencil et al.
4,875,478 A 10/1989 Chen
4,884,566 A 12/1989 Mountz et al.
4,889,526 A 12/1989 Rauscher et al.
4,896,673 A 1/1990 Rose et al.
4,905,698 A 3/1990 Strohl, Jr. et al.
4,923,459 A 5/1990 Nambu
4,931,056 A 6/1990 Ghajar et al.
4,945,305 A 7/1990 Blood 4,945,914 A 8/1990 Allen
4,951,653 A 8/1990 Fry et al.
4,952,214 A 8/1990 Comparetto
4,955,891 A 9/1990 Carol
4,961,422 A 10/1990 Marchosky et al.
4,977,655 A 12/1990 Martinelli
4,989,608 A 2/1991 Ratner
4,991,579 A 2/1991 Allen
5,002,058 A 3/1991 Martinelli
5,005,592 A 4/1991 Cartmell
5,013,317 A 5/1991 Cole et al.
5,016,639 A 5/1991 Allen
5,017,139 A 5/1991 Mushabac
5,027,818 A 7/1991 Bova et al.
5,030,196 A 7/1991 Inoue
5,030,222 A 7/1991 Calandruccio et al.
5,031,203 A 7/1991 Trecha
5,042,486 A 8/1991 Pfeiler et al.
5,047,036 A 9/1991 Koutrovelis
5,050,608 A 9/1991 Watanabe et al.
5,054,492 A 10/1991 Scribner et al.
5,057,095 A 10/1991 Fabian
5,059,789 A 10/1991 Salcudean
5,078,140 A 1/1992 Kwoh
5,079,699 A 1/1992 Tuy et al.
5,086,401 A 2/1992 Glassman et al.
5,094,241 A 3/1992 Allen
5,097,839 A 3/1992 Allen
5,098,426 A 3/1992 Sklar et al.
5,099,845 A 3/1992 Besz et al.
5,099,846 A 3/1992 Hardy
5,105,829 A 4/1992 Fabian et al.
5,107,839 A 4/1992 Houdek et al.
5,107,843 A 4/1992 Aarnio et al.
5,107,862 A 4/1992 Fabian et al.
5,109,194 A 4/1992 Cantaloube
5,116,345 A 5/1992 Jewell et al.
5,119,817 A 6/1992 Allen
5,142,930 A 9/1992 Allen et al.
5,143,076 A 9/1992 Hardy et al.
5,152,288 A 10/1992 Hoenig et al.
5,160,337 A 11/1992 Cosman
5,161,536 A 11/1992 Vikomerson et al.
5,178,164 A 1/1993 Allen
5,178,621 A 1/1993 Cook et al.
5,186,174 A 2/1993 Schlöndorff et al.
5,187,475 A 2/1993 Wagener et al.
5,188,126 A 2/1993 Fabian et al.
5,190,059 A 3/1993 Fabian et al.
5,193,106 A 3/1993 DeSena
5,197,476 A 3/1993 Nowacki et al.
5,197,965 A 3/1993 Cherry et al.
5,198,768 A 3/1993 Keren
5,198,877 A 3/1993 Schulz
5,207,688 A 5/1993 Carol
5,211,164 A 5/1993 Allen
5,211,165 A 5/1993 Dumoulin et al.
5,211,176 A 5/1993 Ishiguro et al.
5,212,720 A 5/1993 Landi et al.
5,214,615 A 5/1993 Bauer
5,219,351 A 6/1993 Teubner et al.
5,222,499 A 6/1993 Allen et al.
5,224,049 A 6/1993 Mushabac
5,228,442 A 7/1993 Imran
5,230,338 A 7/1993 Allen et al.
5,230,623 A 7/1993 Guthrie et al.
5,233,990 A 8/1993 Barnea
5,237,996 A 8/1993 Waldman et al.
5,249,581 A 10/1993 Horbal et al.
5,251,127 A 10/1993 Raab
5,251,635 A 10/1993 Dumoulin et al.
5,253,647 A 10/1993 Takahashi et al.
5,255,680 A 10/1993 Darrow et al.
5,257,636 A 11/1993 White
5,257,998 A 11/1993 Ota et al.
5,261,404 A 11/1993 Mick et al.
5,265,610 A 11/1993 Darrow et al.
5,265,611 A 11/1993 Hoenig et al.
5,269,759 A 12/1993 Hernandez et al.
5,271,400 A 12/1993 Dumoulin et al.
5,273,025 A 12/1993 Sakiyama et al.
5,274,551 A 12/1993 Corby, Jr.
5,279,309 A 1/1994 Taylor et al.
5,285,787 A 2/1994 Machida
5,291,199 A 3/1994 Overman et al.
5,291,889 A 3/1994 Kenet et al.
5,295,483 A 3/1994 Nowacki et al.
5,297,549 A 3/1994 Beatty et al.
5,299,253 A 3/1994 Wessels
5,299,254 A 3/1994 Dancer et al.
5,299,288 A 3/1994 Glassman et al.
5,300,080 A 4/1994 Clayman et al.
5,305,091 A 4/1994 Gelbart et al.
5,305,203 A 4/1994 Raab
5,306,271 A 4/1994 Zinreich et al.
5,307,072 A 4/1994 Jones, Jr.
5,309,913 A 5/1994 Kormos et al.
5,315,630 A 5/1994 Sturm et al.
5,316,024 A 5/1994 Hirschi et al.
5,318,025 A 6/1994 Dumoulin et al.
5,320,111 A 6/1994 Livingston
5,325,728 A 7/1994 Zimmerman et al.
5,325,873 A 7/1994 Hirschi et al.
5,329,944 A 7/1994 Fabian et al.
5,330,485 A 7/1994 Clayman et al.
5,333,168 A 7/1994 Fernandes et al.
5,353,795 A 10/1994 Souza et al.
5,353,800 A 10/1994 Pohndorf et al.
5,353,807 A 10/1994 DeMarco
5,359,417 A 10/1994 Müller et al.
5,368,030 A 11/1994 Zinreich et al.
5,371,778 A 12/1994 Yanof et al.
5,375,596 A 12/1994 Twiss et al.
5,377,678 A 1/1995 Dumoulin et al.
5,383,454 A 1/1995 Bucholz
5,385,146 A 1/1995 Goldreyer
5,385,148 A 1/1995 Lesh et al.
5,386,828 A 2/1995 Owens et al.
5,389,101 A 2/1995 Heilbrun et al.
5,391,199 A 2/1995 Ben-Haim
5,394,457 A 2/1995 Leibinger et al.
5,394,875 A 3/1995 Lewis et al.
5,397,329 A 3/1995 Allen
5,398,684 A 3/1995 Hardy
5,399,146 A 3/1995 Nowacki et al.
5,400,384 A 3/1995 Fernandes et al.
5,402,801 A 4/1995 Taylor
5,408,409 A 4/1995 Glassman et al.
5,413,573 A 5/1995 Koivukangas
5,417,210 A 5/1995 Funda et al.
5,419,325 A 5/1995 Dumoulin et al.
5,423,334 A 6/1995 Jordan
5,425,367 A 6/1995 Shapiro et al.
5,425,382 A 6/1995 Golden et al.
5,426,683 A 6/1995 O'Farrell, Jr. et al.
5,426,687 A 6/1995 Goodall et al.
5,427,097 A 6/1995 Depp
5,429,132 A 7/1995 Guy et al.
5,433,198 A 7/1995 Desai
RE35,025 E 8/1995 Anderton
5,437,277 A 8/1995 Dumoulin et al.
5,443,066 A 8/1995 Dumoulin et al.
5,443,489 A 8/1995 Ben-Haim
5,444,756 A 8/1995 Pai et al.
5,445,144 A 8/1995 Wodicka et al.
5,445,150 A 8/1995 Dumoulin et al.

5,445,166 A 8/1995 Taylor
5,446,548 A 8/1995 Gerig et al.
5,447,154 A 9/1995 Cinquin et al.
5,448,610 A 9/1995 Yamamoto et al.
5,453,686 A 9/1995 Anderson
5,456,718 A 10/1995 Szymaitis
5,457,641 A 10/1995 Zimmer et al.
5,458,718 A 10/1995 Venkitachalam
5,464,446 A 11/1995 Dreessen et al.
5,469,847 A 11/1995 Zinreich et al.
5,478,341 A 12/1995 Cook et al.
5,478,343 A 12/1995 Ritter
5,480,422 A 1/1996 Ben-Haim
5,480,439 A 1/1996 Bisek et al.
5,483,961 A 1/1996 Kelly et al.
5,485,849 A 1/1996 Panescu et al.
5,487,391 A 1/1996 Panescu
5,487,729 A 1/1996 Avellanet et al.
5,487,757 A 1/1996 Truckai et al.
5,490,196 A 2/1996 Rudich et al.
5,494,034 A 2/1996 Schlöndorff et al.
5,503,416 A 4/1996 Aoki et al.
5,513,637 A 5/1996 Twiss et al.
5,514,146 A 5/1996 Lam et al.
5,515,160 A 5/1996 Schulz et al.
5,517,990 A 5/1996 Kalfas et al.
5,531,227 A 7/1996 Schneider
5,531,520 A 7/1996 Grimson et al.
5,542,938 A 8/1996 Avellanet et al.
5,543,951 A 8/1996 Moehrmann
5,546,940 A 8/1996 Panescu et al.
5,546,949 A 8/1996 Frazin et al.
5,546,951 A 8/1996 Ben-Haim
5,551,429 A 9/1996 Fitzpatrick et al.
5,558,091 A 9/1996 Acker et al.
5,566,681 A 10/1996 Manwaring et al.
5,568,384 A 10/1996 Robb et al.
5,568,809 A 10/1996 Ben-haim
5,572,999 A 11/1996 Funda et al.
5,573,533 A 11/1996 Strul
5,575,794 A 11/1996 Walus et al.
5,575,798 A 11/1996 Koutrouvelis
5,583,909 A 12/1996 Hanover
5,588,430 A 12/1996 Bova et al.
5,590,215 A 12/1996 Allen
5,592,939 A 1/1997 Martinelli
5,595,193 A 1/1997 Walus et al.
5,596,228 A 1/1997 Anderton et al.
5,600,330 A 2/1997 Blood
5,603,318 A 2/1997 Heilbrun et al.
5,611,025 A 3/1997 Lorensen et al.
5,617,462 A 4/1997 Spratt
5,617,857 A 4/1997 Chader et al.
5,619,261 A 4/1997 Anderton
5,622,169 A 4/1997 Golden et al.
5,622,170 A 4/1997 Schulz
5,627,873 A 5/1997 Hanover et al.
5,628,315 A 5/1997 Vilsmeier et al.
5,630,431 A 5/1997 Taylor
5,636,644 A 6/1997 Hart et al.
5,638,819 A 6/1997 Manwaring et al.
5,640,170 A 6/1997 Anderson
5,642,395 A 6/1997 Anderton et al.
5,643,268 A 7/1997 Vilsmeier et al.
5,643,286 A 7/1997 Warner et al.
5,645,065 A 7/1997 Shapiro et al.
5,646,524 A 7/1997 Gilboa
5,647,361 A 7/1997 Damadian
5,662,111 A 9/1997 Cosman
5,664,001 A 9/1997 Tachibana et al.
5,674,296 A 10/1997 Bryan et al.
5,676,673 A 10/1997 Ferre et al.
5,681,260 A 10/1997 Ueda et al.
5,682,886 A 11/1997 Delp et al.
5,682,890 A 11/1997 Kormos et al.
5,690,108 A 11/1997 Chakeres
5,694,945 A 12/1997 Ben-Haim
5,695,500 A 12/1997 Taylor et al.
5,695,501 A 12/1997 Carol et al.
5,697,377 A 12/1997 Wittkampf
5,702,406 A 12/1997 Vilsmeier et al.
5,711,299 A 1/1998 Manwaring et al.
5,713,946 A 2/1998 Ben-Haim
5,715,822 A 2/1998 Watkins
5,715,836 A 2/1998 Kliegis et al.
5,718,241 A 2/1998 Ben-Haim et al.
5,727,552 A 3/1998 Ryan
5,727,553 A 3/1998 Saad
5,729,129 A 3/1998 Acker
5,730,129 A 3/1998 Darrow et al.
5,730,130 A 3/1998 Fitzpatrick et al.
5,732,703 A 3/1998 Kalfas et al.
5,735,278 A 4/1998 Hoult et al.
5,738,096 A 4/1998 Ben-Haim
5,740,802 A 4/1998 Nafis et al.
5,741,214 A 4/1998 Ouchi et al.
5,742,394 A 4/1998 Hansen
5,744,953 A 4/1998 Hansen
5,748,767 A 5/1998 Raab
5,749,362 A 5/1998 Funda
5,749,835 A 5/1998 Glantz
5,752,513 A 5/1998 Acker et al.
5,755,725 A 5/1998 Druais
RE35,816 E 6/1998 Schulz
5,758,667 A 6/1998 Slettenmark
5,762,064 A 6/1998 Polyani
5,767,669 A 6/1998 Hansen et al.
5,767,960 A 6/1998 Orman
5,769,789 A 6/1998 Wang et al.
5,769,843 A 6/1998 Abela et al.
5,769,861 A 6/1998 Vilsmeier
5,772,594 A 6/1998 Barrick
5,775,322 A 7/1998 Silverstein et al.
5,776,064 A 7/1998 Kalfas et al.
5,782,765 A 7/1998 Jonkman
5,787,886 A 8/1998 Kelly et al.
5,792,055 A 8/1998 McKinnon
5,795,294 A 8/1998 Luber et al.
5,797,849 A 8/1998 Vesely et al.
5,799,055 A 8/1998 Peshkin et al.
5,799,099 A 8/1998 Wang et al.
5,800,352 A 9/1998 Ferre et al.
5,800,535 A 9/1998 Howard, III
5,802,719 A 9/1998 O'Farrell, Jr., et al.
5,803,089 A 9/1998 Ferre et al.
5,807,252 A 9/1998 Hassfeld et al.
5,810,008 A 9/1998 Dekel et al.
5,810,712 A 9/1998 Dunn
5,810,728 A 9/1998 Kuhn
5,810,735 A 9/1998 Halperin et al.
5,817,106 A 10/1998 Real
5,820,553 A 10/1998 Hughes
5,823,192 A 10/1998 Kalend et al.
5,823,958 A 10/1998 Truppe
5,828,725 A 10/1998 Levinson
5,828,770 A 10/1998 Leis et al.
5,829,444 A 11/1998 Ferre et al.
5,831,260 A 11/1998 Hansen
5,833,608 A 11/1998 Acker
5,833,627 A 11/1998 Shmulewitz et al.
5,833,709 A 11/1998 Rise et al.
5,834,759 A 11/1998 Glossop
5,836,954 A 11/1998 Heilbrun et al.
5,840,024 A 11/1998 Taniguchi et al.
5,840,025 A 11/1998 Ben-Haim
5,843,076 A 12/1998 Webster, Jr. et al.

5,848,967 A 12/1998 Cosman
5,851,183 A 12/1998 Bucholz
5,865,846 A 2/1999 Bryan et al.
5,868,674 A 2/1999 Glowinski et al.
5,868,675 A 2/1999 Henrion et al.
5,871,445 A 2/1999 Bucholz
5,871,455 A 2/1999 Ueno
5,871,487 A 2/1999 Warner et al.
5,873,822 A 2/1999 Ferre et al.
5,882,304 A 3/1999 Ehnholm et al.
5,884,410 A 3/1999 Prinz
5,889,834 A 3/1999 Vilsmeier et al.
5,891,034 A 4/1999 Bucholz
5,891,157 A 4/1999 Day et al.
5,904,691 A 5/1999 Barnett et al.
5,907,395 A 5/1999 Schulz et al.
5,913,820 A 6/1999 Bladen et al.
5,920,395 A 7/1999 Schulz
5,921,992 A 7/1999 Costales et al.
5,923,727 A 7/1999 Navab
5,928,248 A 7/1999 Acker
5,938,603 A 8/1999 Ponzi
5,938,694 A 8/1999 Jaraczewski et al.
5,947,980 A 9/1999 Jensen et al.
5,947,981 A 9/1999 Cosman
5,950,629 A 9/1999 Taylor et al.
5,951,475 A 9/1999 Gueziec et al.
5,951,571 A 9/1999 Audette
5,954,647 A 9/1999 Bova et al.
5,957,844 A 9/1999 Dekel et al.
5,964,796 A 10/1999 Imran
5,967,980 A 10/1999 Ferre et al.
5,967,982 A 10/1999 Barnett
5,968,047 A 10/1999 Reed
5,971,997 A 10/1999 Guthrie et al.
5,976,156 A 11/1999 Taylor et al.
5,980,535 A 11/1999 Barnett et al.
5,983,126 A 11/1999 Wittkampf
5,984,930 A * 11/1999 Maciunas et al. ........... 606/130
5,987,349 A 11/1999 Schulz
5,987,960 A 11/1999 Messner et al.
5,999,837 A 12/1999 Messner et al.
5,999,840 A 12/1999 Grimson et al.
6,001,130 A 12/1999 Bryan et al.
6,006,126 A 12/1999 Cosman
6,006,127 A 12/1999 Van Der Brug et al.
6,013,087 A 1/2000 Adams et al.
6,014,580 A 1/2000 Blume et al.
6,016,439 A 1/2000 Acker
6,019,725 A 2/2000 Vesely et al.
6,021,343 A 2/2000 Foley et al.
6,024,695 A 2/2000 Greenberg et al.
6,050,724 A 4/2000 Schmitz et al.
6,059,718 A 5/2000 Taniguchi et al.
6,063,022 A 5/2000 Ben-Haim
6,071,288 A * 6/2000 Carol et al. ................. 606/130
6,073,043 A 6/2000 Schneider
6,076,008 A 6/2000 Bucholz
6,081,288 A * 6/2000 Kojima ....................... 347/221
6,096,050 A 8/2000 Audette
6,104,944 A 8/2000 Martinelli
6,118,845 A 9/2000 Simon et al.
6,122,538 A 9/2000 Sliwa, Jr. et al.
6,122,541 A 9/2000 Cosman et al.
6,131,396 A 10/2000 Duerr et al.
6,139,183 A 10/2000 Graumann
6,147,480 A 11/2000 Osadchy et al.
6,149,592 A 11/2000 Yanof et al.
6,156,067 A 12/2000 Bryan et al.
6,161,032 A 12/2000 Acker
6,165,181 A 12/2000 Heilbrun et al.
6,167,296 A 12/2000 Shahidi
6,172,499 B1 1/2001 Ashe
6,175,756 B1 1/2001 Ferre et al.
6,178,345 B1 1/2001 Vilsmeier et al.
6,194,639 B1 2/2001 Botella et al.
6,201,387 B1 3/2001 Govari
6,203,497 B1 3/2001 Dekel et al.
6,211,666 B1 4/2001 Acker
6,223,067 B1 4/2001 Vilsmeier
6,233,476 B1 5/2001 Strommer et al.
6,246,231 B1 6/2001 Ashe
6,259,942 B1 7/2001 Westermann et al.
6,273,896 B1 8/2001 Franck et al.
6,285,902 B1 9/2001 Kienzle, III et al.
6,298,262 B1 10/2001 Franck et al.
6,314,310 B1 11/2001 Ben-Haim et al.
6,327,491 B1 * 12/2001 Franklin et al. ............ 600/429
6,332,089 B1 12/2001 Acker et al.
6,341,231 B1 1/2002 Ferre et al.
6,351,659 B1 2/2002 Vilsmeier
6,381,485 B1 4/2002 Hunter et al.
6,424,856 B1 7/2002 Vilsmeier et al.
6,427,314 B1 8/2002 Acker
6,428,547 B1 8/2002 Vilsmeier et al.
6,434,415 B1 8/2002 Foley et al.
6,437,567 B1 8/2002 Schenck et al.
6,445,943 B1 9/2002 Ferre et al.
6,470,207 B1 10/2002 Simon et al.
6,474,341 B1 11/2002 Hunter et al.
6,478,802 B2 11/2002 Kienzle, III et al.
6,484,049 B1 11/2002 Seeley et al.
6,490,475 B1 12/2002 Seeley et al.
6,493,573 B1 12/2002 Martinelli et al.
6,498,944 B1 12/2002 Ben-Haim et al.
6,499,488 B1 12/2002 Hunter et al.
6,516,046 B1 2/2003 Fröhlich et al.
6,527,443 B1 3/2003 Vilsmeier et al.
6,551,325 B2 4/2003 Neubauer et al.
6,584,174 B2 6/2003 Schubert et al.
6,609,022 B2 8/2003 Vilsmeier et al.
6,611,700 B1 8/2003 Vilsmeier et al.
6,640,128 B2 10/2003 Vilsmeier et al.
6,694,162 B2 2/2004 Hartlep
6,701,179 B1 3/2004 Martinelli et al.
2001/0007918 A1 7/2001 Vilsmeier et al.
2001/0027271 A1 10/2001 Franck et al.
2002/0095081 A1 7/2002 Vilsmeier
2004/0024309 A1 2/2004 Ferre et al.

FOREIGN PATENT DOCUMENTS

DE 3042343 A1 6/1982
DE 35 08730 3/1985
DE 37 17 871 5/1987
DE 38 38011 11/1988
DE 3831278 A1 3/1989
DE 42 13 426 4/1992
DE 42 25 112 7/1992
DE 4233978 C1 4/1994
DE 197 15 202 4/1997
DE 197 15 202 A1 4/1997
DE 197 47 427 10/1997
DE 197 47 427 A1 10/1997
DE 197 51 761 11/1997
DE 198 32 296 7/1998
DE 10085137 11/2002
EP 0 062 941 3/1982
EP 0 119 660 9/1984
EP 0 155 857 1/1985
EP 0 319 844 A1 1/1988
EP 0 359 773 B1 5/1988
EP 0 207 452 A2 6/1988
EP 0 326 768 12/1988
EP 0 326 768 A2 12/1988
EP 0419729 A1 9/1989

| | | | |
|---|---|---|---|
| EP | 0350996 | A1 | 1/1990 |
| EP | 0 651 968 | A1 | 8/1990 |
| EP | 0 427 358 | | 10/1990 |
| EP | 0 427 358 | A1 | 10/1990 |
| EP | 0 456 103 | | 5/1991 |
| EP | 0 469 966 | A1 | 7/1991 |
| EP | 0 581 704 | B1 | 7/1993 |
| EP | 0655138 | B1 | 8/1993 |
| EP | 0894473 | A2 | 1/1995 |
| EP | 0 908 146 | | 10/1998 |
| EP | 0 930 046 | | 10/1998 |
| EP | 0 919 202 | A2 | 6/1999 |
| EP | 0 919 203 | A2 | 6/1999 |
| FR | 2417970 | | 2/1979 |
| FR | 2 618 211 | | 7/1987 |
| GB | 2 094 590 | | 2/1982 |
| GB | 2 164 856 | | 10/1984 |
| JP | 61-94639 | | 10/1984 |
| JP | 62-327 | | 6/1985 |
| JP | 63-240851 | | 3/1987 |
| JP | 3-267054 | | 3/1990 |
| JP | 2765738 | | 4/1998 |
| WO | WO 88/0915 | | 12/1988 |
| WO | WO 88/09151 | | 12/1988 |
| WO | WO 89/05123 | | 6/1989 |
| WO | WO 90/05494 | | 11/1989 |
| WO | WO 91/03982 | | 4/1991 |
| WO | WO 91/04711 | | 4/1991 |
| WO | WO 91/07726 | | 5/1991 |
| WO | WO 92/03090 | | 3/1992 |
| WO | WO 92/06645 | | 4/1992 |
| WO | WO 94/04938 | | 3/1994 |
| WO | WO 95/07055 | | 9/1994 |
| WO | WO 94/23647 | | 10/1994 |
| WO | WO 94/24933 | | 11/1994 |
| WO | WO 96/32059 | | 11/1995 |
| WO | WO 96/11624 | | 4/1996 |
| WO | WO 96/32059 | | 10/1996 |
| WO | WO 97/49453 | | 6/1997 |
| WO | WO 97/36192 | | 10/1997 |
| WO | WO 99/23956 | | 11/1997 |
| WO | WO 97/49453 | | 12/1997 |
| WO | WO 98/08554 | | 3/1998 |
| WO | WO 98/38908 | | 9/1998 |
| WO | WO 99/15097 | | 9/1998 |
| WO | WO 99/21498 | | 10/1998 |
| WO | WO 99/27839 | | 12/1998 |
| WO | WO 99/33406 | | 12/1998 |
| WO | WO 99/38449 | | 1/1999 |
| WO | WO 99/15097 | | 4/1999 |
| WO | WO 99/52094 | | 4/1999 |
| WO | WO 99/26549 | | 6/1999 |
| WO | WO 99/29253 | | 6/1999 |
| WO | WO 99/37208 | | 7/1999 |
| WO | WO 99/60939 | | 12/1999 |
| WO | WO 01/30437 | A1 | 5/2001 |

OTHER PUBLICATIONS

Moran, et al., "Central Nervous System Lesions Biopsied or Treated by CT-Guided Needle Placement, Radiology," Jun. 1979, 681-686, vol. 131, No. 3.

Bergstrom, et al., "Stereotaxic Computer Tomography," Am J. Roentgenol, 1976, 167-170, vol. 127.

Troccaz, et al., "The Use of Localizers, Robots and Synergistic Devices in CAS."

Kondziolka, et al., "Guided Neurosurgery Using the ISG Viewing Wand®," Contemporary Neurosurgery, 1995, 1-6, vol. 17, No. 8.

Olivier, et al., "Frameless Stereotaxy for Surgery of the Epilepsies: Preliminary Experience." Journal of Neurosurgery, Oct. 1994, 629-633, vol. 81, No. 4.

Smith, et al., "The Neurostation™-A Highly Accurate, Minimally Invasive Solution to Frameless Stereotactic Neurosurgery, Computerized Medical Imaging and Graphics," 1994, 247, 274-277, vol. 18, No. 4.

Reinhardt, et al., "Sonic Stereometry in Microsurgical Procedures for Deep-Seated Brain Tumors and Vascular Malformations," Neurosurgery, Jan. 1993, 51-57, vol. 32, No. 1.

Reinhardt, "Neuronavigation: A Ten-Year Review," Neurosurgery, 329-341.

Bucholz, et al., "Intraoperative Localization Using a Three Dimensional Optical Digitizer," Proceedings of Clinical Applications of Modern Imaging Technology, Jan. 1993, 312-322, vol. 1894.

PixSys, "Alignment Procedure for the PixSys Two-Emitter Offset Probe for the SAC GP-8-3d Sonic Digitizer," PixSys, Boulder, CO.

PixSys, "3-D Digitizing Accessories," Pixsys, Boulder, CO.

Adams, et al., "Orientation Aid for Head and Neck Surgeons" Innov. Tech. Biol. Med., 1992, vol. 13, No. 4.

Reinhardt, et al., "Microsurgical Removal of Deep-Seated Vascular Malformations Using Sonar Stereometry," Ultraschall in Med., 1991, 80-84, vol. 12.

Pelizzari, et al., "Interactive 3D Patient-Image Registration, Information Processing in Medical Imaging," 1991, 132-141, Springer-Verlag Berlin Heidelberg, Germany.

Mazier, et al., "Computer Assisted Interventionist Imaging: Application to the Vertebral Column Surgery," Annual International Conference of the IEEE Engineering in Medicine and Biology Society, 1990, 430-431, vol. 12, No. 1.

Krybus, et al., "Navigation Support for Surgery by Means of Optical Position Detection," 362-366.

Rosenbaum, et al., "Computerized Tomography Guided Stereotaxis: A New Approach," Applied Neurophysiology, 1980, 172-173, vol. 43, No. 3-5.

Boethius, et al., "Stereotaxic Computerized Tomography with GE 8800 Scanner," J. Neurosurg., 1980, 794-800, vol. 52, No. 6.

Yeates, et al., "Simplified and Accurate CT-Guided Needle Biopsy of Central Nervous System Lesions," J. Neurosurg., 1982, 390-393, vol. 57, No. 3.

Heilbrun, "Computed Tomography-Guided Stereotactic System," Clinical Neurosurgery, 564-581.

Heilbrun, et al., "Preliminary Experience with Brown-Roberts-Wells (BRW) Computerized Tomography Stereotaxic Guidance System," J. Neurosurg., 1983, 217-222, vol. 59.

La Vallee, "A New System for Computer Assisted Neurosurgery," IEEE Engineering in Medicine & Biology Society 11th Annual International Conference, 1989, 926-927.

La Vallee, "Computer Assisted Driving of a Needle into the Brain," Computer Assisted Radiology, 1989, 416-420, Springer-Verlag.

La Vallee, "Adaptation de la Methodologie a Quelques Applications Cliniques," Chapter VI, pp. 133-148.

"Prestige Cervical Disc System Surgical Technique", 12 pgs.

Barrick et al., "Prophylactic Intramedullary Fixation of the Tibia for Stress Fracture in a Professional Athlete," Journal of Orthopaedic Trauma, vol. 6, No. 2, pp. 241-244 (1992).

Barrick et al., "Technical Difficulties with the Brooker-Wills Nail in Acute Fractures of the Femur," Journal of Orthopaedic Trauma, vol. 6, No. 2, pp. 144-150 (1990).

Barrick, "Distal Locking Screw Insertion Using a Cannulated Drill Bit: Technical Note," Journal of Orthopaedic Trauma, vol. 7, No. 3, 1993, pp. 248-251.

Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.

Benzel et al., "Magnetic Source Imaging: a Review of the Magnes System of Biomagnetic Technologies Incorporated," Neurosurgery, vol. 33, No. 2 (Aug. 1993), pp. 252-259.

Bouazza-Marouf et al.; "Robotic-Assisted Internal Fixation of Femoral Fractures", IMECHE., pp. 51-58 (1995).

Brack et al., "Accurate X-ray Based Navigation in Computer-Assisted Orthopedic Surgery," CAR '98, pp. 716-722.

Bryan, "Bryan Cervical Disc System Single Level Surgical Technique", Spinal Dynamics, 2002, pp. 1-33.

Bucholz et al., "Variables affecting the accuracy of stereotactic localizationusing computerized tomography," Journal of Neurosurgery, vol. 79, Nov. 1993, pp. 667-673.
Champleboux et al., "Accurate Calibration of Cameras and Range Imaging Sensors: the NPBS Method," IEEE International Conference on Robotics and Automation, Nice, France, May, 1992.
Champleboux, "Utilisation de Fonctions Splines pour la Mise au Point D'un Capteur Tridimensionnel sans Contact," Quelques Applications Medicales, Jul. 1991.
Cinquin et al., "Computer Assisted Medical Interventions," IEEE Engineering in Medicine and Biology, May/Jun. 1995, pp. 254-263.
Cinquin et al., "Computer Assisted Medical Interventions," International Advanced Robotics Programme, Sep. 1989, pp. 63-65.
Clarysse et al., "A Computer-Assisted System for 3-D Frameless Localization in Stereotaxic MRI," IEEE Transactions on Medical Imaging, vol. 10, No. 4, Dec. 1991, pp. 523-529.
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.
Foley et al., "Image-guided Intraoperative Spinal Localization," Intraoperative Neuroprotection, Chapter 19, 1996, pp. 325-340.
Foley, "The StealthStation: Three-Dimensional Image-Interactive Guidance for the Spine Surgeon," Spinal Frontiers, Apr. 1996, pp. 7-9.
Gildenberg et al., "Calculation of Stereotactic Coordinates from the Computed Tomographic Scan," Neurosurgery, vol. 10, No. 5, May 1982, pp. 580-586.
Gonzalez, "Digital Image Fundamentals," Digital Image Processing, Second Edition, 1987, pp. 52-54.
Gottesfeld Brown et al., "Registration of Planar Film Radiographs with Computer Tomography," Proceedings of MMBIA, Jun. '96, pp. 42-51.
Gueziec et al., "Registration of Computed Tomography Data to a Surgical Robot Using Fluoroscopy: A Feasibility Study," Computer Science/Mathematics, Sep. 27, 1996, 6 pages.
Hamadeh et al, "Kinematic Study of Lumbar Spine Using Functional Radiographies and 3D/2D Registration," TIMC UMR 5525—IMAG.
Hamadeh et al., "Automated 3-Dimensional Computed Tomographic and Fluorscopic Image Registration," Computer Aided Surgery (1998), 3:11-19.
Hamadeh et al., "Towards Automatic Registration Between CT and X-ray Images: Cooperation Between 3D/2D Registration and 2D Edge Detection," MRCAS '95, pp. 39-46.
Hatch, "Reference-Display System for the Integration of CT Scanning and the Operating Microscope," Thesis, Thayer School of Engineering, Oct. 1984, pp. 1-189.
Henderson et al., "An Accurate and Ergonomic Method of Registration for Image-guided Neurosurgery," Computerized Medical Imaging and Graphics, vol. 18, No. 4, Jul.-Aug. 1994, pp. 273-277.
Hoerenz, "The Operating Microscope I. Optical Principles, Illumination Systems, and Support Systems," Journal of Microsurgery, vol. 1, 1980, pp. 364-369.
Hofstetter et al., "Fluoroscopy Based Surgical Navigation—Concept and Clinical Applications," Computer Assisted Radiology and Surgery, 1997, pp. 956-960.
Horner et al., "A Comparison of CT-Stereotaxic Brain Biopsy Techniques," Investigative Radiology, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
Jacques et al., "A Computerized Microstereotactic Method to Approach, 3-Dimensionally Reconstruct, Remove and Adjuvantly Treat Small CNS Lesion," Applied Neurophysiology, vol. 43, 1980, pp. 176-182.
Jacques et al., "Computerized three-dimensional stereotaxic removal of small central nervous system lesion in patients," J. Neurosurg., vol. 53, Dec. 1980, pp. 816-820.
Joskowicz et al., "Computer-Aided Image-Guided Bone Fracture Surgery: Concept and Implementation," CAR '98, pp. 710-715.
Kelly et al., "Computer-assisted stereotaxic laser resection of intra-axial brain neoplasms," Journal of Neurosurgery, vol. 64, Mar. 1986, pp. 427-439.
Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee et al, "Matching 3-D Smooth Surfaces with their 2-D Projections using 3-D Distance Maps," SPIE, vol. 1570, Geometric Methods in Computer Vision, 1991, pp. 322-336.
Lavallee et al., "Computer Assisted Interventionist Imaging: The Instance of Stereotactic Brain Surgery," North-Holland MEDINFO 89, Part 1, 1989, pp. 613-617.
Lavallee et al., "Computer Assisted Spine Surgery: A Technique For Accurate Transpedicular Screw Fixation Using CT Data and a 3-D Optical Localizer," TIMC, Faculte de Medecine de Grenoble.
Lavallee et al., "Image guided operating robot: a clinical application in stereotactic neurosurgery," Proceedings of the 1992 IEEE Internation Conference on Robotics and Automation, May 1992, pp. 618-624.
Lavallee et al., "Matching of Medical Images for Computed and Robot Assisted Surgery," IEEE EMBS, Orlando, 1991.
Leksell et al., "Stereotaxis and Tomography—A Technical Note," ACTA Neurochirurgica, vol. 52, 1980, pp. 1-7.
Lemieux et al., "A Patient-to-Computed-Tomography Image Registration Method Based on Digitally Reconstructed Radiographs," Med. Phys. 21 (11), Nov. 1994, pp. 1749-1760.
Levin et al., "The Brain: Integrated Three-dimensional Display of MR and PET Images," Radiology, vol. 172, No. 3, Sep. 1989, pp. 783-789.
Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.
Pelizzari et al., "Accurate Three-Dimensional Registration of CT, PET, and/or MR Images of the Brain," Journal of Computer Assisted Tomography, Jan./Feb. 1989, pp. 20-26.
Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).
Pelizzari et al., No. 528—"Three Dimensional Correlation of PET, CT and MRI Images," The Journal of Nuclear Medicine, vol. 28, No. 4, Apr. 1987, p. 682.
Phillips et al., "Image Guided Orthopaedic Surgery Design and Analysis," Trans Inst. MC, vol. 17, No. 5, 1995, pp. 251-264.
Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.
Reinhardt et al., "CT-Guided 'Real Time' Stereotaxy," ACTA Neurochirurgica, 1989.
Roberts et al., "A frameless stereotaxic integration of computerized tomographic imaging and the operating microscope," J. Neurosurg., vol. 65, Oct. 1986, pp. 545-549.
Sautot, "Vissage Pediculaire Assiste Par Ordinateur," Sep. 20, 1994.
Schueler et al., "Correction of Image Intensifier Distortion for Three-Dimensional X-Ray Angiography," SPIE Medical Imaging 1995, vol. 2432, pp. 272-279.
Selvik et al., "A Roentgen Stereophotogrammetric System," Acta Radiologica Diagnosis, 1983, pp. 343-352.
Shelden et al., "Development of a computerized microsteroetaxic method for localization and removal of minute CNS lesions under direct 3-D vision," J. Neurosurg., vol. 52, 1980, pp. 21-27.
Smith et al., "Computer Methods for Improved Diagnostic Image Display Applied to Stereotactic Neurosurgery," Automedical, vol. 14, 1992, pp. 371-382 (4 unnumbered pages).
Smith et al., "the Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

The Laitinen Stereotactic System, E2-E6.
Viant et al., "A Computer Assisted Orthopaedic System for Distal Locking of Intramedullary Nails," Proc. of MediMEC '95, Bristol, 1995, pp. 86-91.
Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.
Watanabe, "Neuronavigator," Igaku-no-Ayumi, vol. 137, No. 6, May 10, 1986, pp. 1-4.
Weese et al., "An Approach to 2D/3D Registration of a Vertebra in 2D X-ray Fluoroscopies with 3D CT Images," pp. 119-128.
Germano, "Instrumentation, Technique and Technology", Neurosurgery, vol. 37, No. 2, Aug. 1995, pp. 348-350.
Merloz, et al., "Computer Assisted Spine Surgery", Clinical Assisted Spine Surgery, No. 337, pp. 86-96.
Hatch, et al., "Reference-Display System for the Integration of CT Scanning and the Operating Microscope", Proceedings of the Eleventh Annual Northeast Bioengineering Conference, Mar. 14-15, 1985, pp. 252-254.
Adams et al., Computer-Assisted Surgery, IEEE Computer Graphics & Applications, pp. 43-51, (May 1990).
Bergstrom et al. Stereotaxic Computed Tomography, Am. J. Roentgenol, vol. 127 pp. 167-170 (1976).
Brown, R., M.D., A Stereotactic Head Frame for Use with CT Body Scanners, Investigative Radiology © J.B. Lippincott Company, pp. 300-304 (Jul.-Aug. 1979).
Bucholz, R.D., et al. Image-guided surgical techniques for infections and trauma of the central nervous system, Neurosurg. Clinics of N.A., vol. 7, No. 2, pp. 187-200 (1996).
Bucholz, R.D., et al., A Comparison of Sonic Digitizers Versus Light Emitting Diode-Based Localization, Interactive Image-Guided Neurosurgery, Chapter 16, pp. 179-200 (1993).
Bucholz, R.D., et al., Intraoperative localization using a three dimensional optical digitizer, SPIE—The Intl. Soc. for Opt. Eng., vol. 1894, pp. 312-322 (Jan. 17-19, 1993).
Bucholz, R.D. et al., Intraoperative Ultrasonic Brain Shift Monitor and Analysis, Stealth Station Marketing Brochure (2 pages) (undated).
Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).
Cutting M.D. et al., Optical Tracking of Bone Fragments During Craniofacial Surgery, Second Annual International Symposium on Medical Robotics and Computer Assisted Surgery, pp. 221-225, (Nov. 1995).
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, C.C., et al., Intracranial Neurosurgery Guided by Functional Imaging, Surg. Neurol., vol. 42, pp. 523-530 (1994).
Galloway, R.L., Jr. et al, Optical localization for interactive, image-guided neurosurgery, SPIE, vol. 2164, pp. 137-145 (undated.
Galloway, R.L., et al., Interactive Image-Guided Neurosurgery, IEEE Trans. on Biomed. Eng., vol. 89, No. 12, pp. 1226-1231 (1992).
Gomez, C.R., et al., Transcranial Doppler Ultrasound Following Closed Head Injury: Vasospasm or Vasoparalysis?, Surg. Neurol., vol. 35, pp. 30-35 (1991).
Grimson, W.E.L., An Automatic Registration Method for Frameless Sterotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).
Guthrie, B.L., Graphic-Interactive Cranial Surgery: The Operating Arm System, Handbook of Stereotaxy Using the CRW Apparatus, Chapter 13, pp. 193-211 (undated.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
Heilbrun, M.P., Computed Tomography—Guided Stereotactic Systems, Clinical Neurosurgery, Chapter 31, pp. 564-581 (1983).
Heilbrun, M.P., et al., Stereotactic Localization and Guidance Using a Machine Vision Technique, Sterotact & Funct. Neurosurg., Proceed, of the Mtg. of the Amer. Soc. for Sterot. and Funct. Neurosurg. (Pittsburgh, PA) vol. 58, pp. 94-98 (1992).
Kall, B., The Impact of Computer and Imgaging Technology on Stereotactic Surgery, Proceedings of the Meeting of the American Society for Stereotactic and Functional Neurosurgery, pp. 10-22 (1987).
Kato, A., et al., A frameless, armless navigational system for computer-assisted neurosurgery, J. Neurosurg., vol. 74, pp. 845-849 (May 1991).
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Computer-Directed Stereotactic Resection of Brain Tumors, Neurologica Operative Atlas, vol. 1, No. 4, pp. 299-313 (1991).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Klimek, L., et al., Long-Term Experience with Different Types of Localization Systems, in Skull-Bases Surgery, Ear, Nose & Throat Surgery, Chapter 51, pp. 635-638 (undated).
Kosugi, Y., et al., An Articulated Neurosurgical Navigation System Using MRI and CT Images, IEEE Trans. on Biomed, Eng. vol. 35, No. 2, pp. 147-152 (Feb. 1988).
Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).
Kwoh, Y.S., Ph.D., et al., A New Computerized Tomographic-Aided Robotic Stereotaxis System, Robotics Age, vol. 7, No. 6, pp. 17-22 (Jun. 1985).
Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Lavalle, S., et al., Computer Assisted Medical Interventions, NATO ASI Series, vol. F 60, 3d Imaging in Medic., pp. 301-312 (1990).
Leavitt, D.D., et al., Dynamic Field Shaping to Optimize Stereotactic Radiosurgery, I.J. Rad. Onc. Biol. Physc., vol. 21, pp. 1247-1255 (1991).
Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).
McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).
Ng, W.S. et al., Robotic Surgery—A First-Hand Experience in Transurethral Resection of the Prostate Surgery, IEEE Eng. in Med. and Biology, pp. 120-125 (Mar. 1993).
Penn, R.D., et al., Stereotactic Surgery with Image Processing of Computerized Tomographic Scans, Neurosurgery, vol. 3, No. 2, pp. 157-163 (Sep.-Oct. 1978).
Pixsys, 3-D Digitizing Accessories, by Pixsys (marketing brochure)(undated) (2 pages).

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Entfernung tiefliegender Gefäβmiβbildungen mit Hilfe der Sonar-Stereometrie (Microsurgical Removal of Deep-Seated Vascular Malformations Using Sonar Stereometry). Ultraschall in Med. 12, pp. 80-83 (1991).

Reinhardt, Hans. F., Neuronavigation: A Ten-Year Review, Neurosurgery, pp. 329-341 (undated).

Simon, D.A., Accuracy Validation in Image-Guided Orthopaedic Surgery, Second Annual Intl. Symp. on Med. Rob. an Comp-Assisted surgery, MRCAS '95, pp. 185-192 (undated).

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

* cited by examiner

INSTRUMENT GUIDANCE METHOD AND SYSTEM FOR IMAGE GUIDED SURGERY

RELATED APPLICATION

This application is a continuation of U.S. patent application Ser. No. 09/557,004 filed on Apr. 20, 2000, which is now U.S. Pat. No. 6,491,699; and this application claims priority benefit to U.S. Provisional Application No. 60/130,118 entitled "Instrument Guidance Method and System For Image Guided Surgery", filed on Apr. 20, 1999. The disclosures of the above applications are incorporated herein by reference.

BACKGROUND OF THE INVENTION

1. Field of the Invention

The present invention relates generally to computer assisted image guided medical and surgical navigation systems that generate images during medical and surgical procedures indicating the relative position of various body parts, surgical implants, and instruments. In particular, the present invention relates to a reference frame and instrument guide frame for use in an image guided surgery navigation system.

2. Background of Related Art

In image guided medical and surgical procedures, images, obtained either preoperatively or intraoperatively (i.e., prior to or during a medical or surgical procedure), are used to aid a doctor in guiding a surgical instrument. Computer assisted image guided medical and surgical navigation systems are known and are disclosed, for example, in U.S. Pat. No. 5,383,454 to Bucholz; U.S. Pat. No. 5,891,034 to Bucholz; U.S. Pat. No. 5,851,183 to Bucholz; U.S. Pat. No. 5,871,445 to Bucholz; PCT Application No. PCT/US 94/04530 (Publication No. WO 94/24933) to Bucholz; PCT Application No. PCT/US 95/12984 (Publication No. WO 96/11624) to Bucholz et al.; and U.S. patent application Ser. No. 08/623,956 to Foley et al., the entire disclosures of which are incorporated herein by reference.

In general, these image guided systems use images of a body part or other surgical object, obtained from a scan, such as CT or MRI scan, taken before surgery to generate images on a display screen during surgery. The images of the body are correlated with a synthesized image of a surgical instrument and are used to produce, on a display screen, a real-time representation of the surgical instrument used by a surgeon with respect to the body. Prior to the scan of the body to produce body images, markers such as fiducial scanning markers are placed on the parts of the body to be scanned in order to produce fiducial image points on the scanned part of the body. The locations of the fiducial markers represented on the scanned image are correlated with the fiducial scanning markers on the body to provide a coordinate registration to be used by the computer system in determining the relative location of the various objects that the computer tracks. The surgical instrument is also registered with respect to the fiducial scanning markers, as known to those skilled in the art, by positioning the surgical instrument at each of scanning markers and recording the relative location of the instrument and markers.

During surgery, the relative locations of the body part being examined and the surgical instruments are displayed on a display screen of the computer system by detecting the location of tracking markers on the instruments or body. An array of sensors, such as cameras, are used to track the location of the tracking markers, which in turn are interpreted by the computer system to produce images on the display screen that correspond to the positions of the body part and surgical instruments. Such tracking markers can include, for example, LED arrays mounted on the body part and on an instrument.

SUMMARY

Generally, the present invention is directed to a method and system for aligning a surgical guide instrument over a burr hole in a patient's body. More particularly, the present invention is directed to a stand-alone instrument guidance unit that is attachable to a patient's body, particularly the skull. The guidance unit itself is equipped with tracking devices to permit a computer assisted image guided surgery system to track the position of the unit. Adjustments of a surgical instrument can be made in x, y, z and angular directions using the system and method of the present invention.

In one aspect of the present invention, an instrument guide unit includes an instrument guide for guiding a surgical instrument into the body of a patient and a base unit operative to be secured to the body in an area in which surgery is to occur. The base unit is coupled to the instrument guide. An adjustment mechanism, coupled to the base unit and the instrument guide, is operative to adjust the instrument guide in lateral directions with respect the surface of the area. The base unit may have tracking markers attached thereto.

The adjustment mechanism is operative to adjust the instrument guide in x and y directions. The adjustment mechanism includes an x direction control mechanism for adjusting the instrument in an x direction and a y direction control mechanism for adjusting the instrument in a y direction. The y direction control mechanism may be coupled to the x direction control The instrument adjustment unit may include a plate having a first attachment member for coupling to the adjustment mechanism. The adjustment member includes a mounting base that is operative to be coupled to the plate by the first attachment member. The plate has a second attachment member extending therefrom for anchoring in the body of the person at the area. An opening is defined through the first and second attachment members such that a surgical instrument may pass and extend through the first and second attachment members. The first attachment member has threaded grooves for screwing into a corresponding attachment member of the mounting base and the second attachment member has threaded grooves for screwing into the body at the area.

Another aspect of the present invention provides a method for guiding a surgical instrument for use in image guided surgery. The method includes determining the location of a stand-alone instrument guidance unit attached to the skull of a patient by sensing signals from tracking markers coupled to the instrument guidance unit and determining the location and orientation of an instrument guide of the guidance unit. This method also includes displaying image representations of the body part of interest relative to a trajectory line defined by the orientation of the instrument guide during a surgical procedure.

The method may also include determining the orientation of the instrument guide as the instrument guide is pivoted. The orientation of the instrument guide is determined by detecting the location of tracking markers on the instrument guide. The x and y coordinate positions of the instrument guide may be adjusted with respect to the body part, such as the skull. The z coordinate position of a surgical instrument inserted in the instrument guide may also be adjusted.

DETAILED DESCRIPTION

Figure 1:
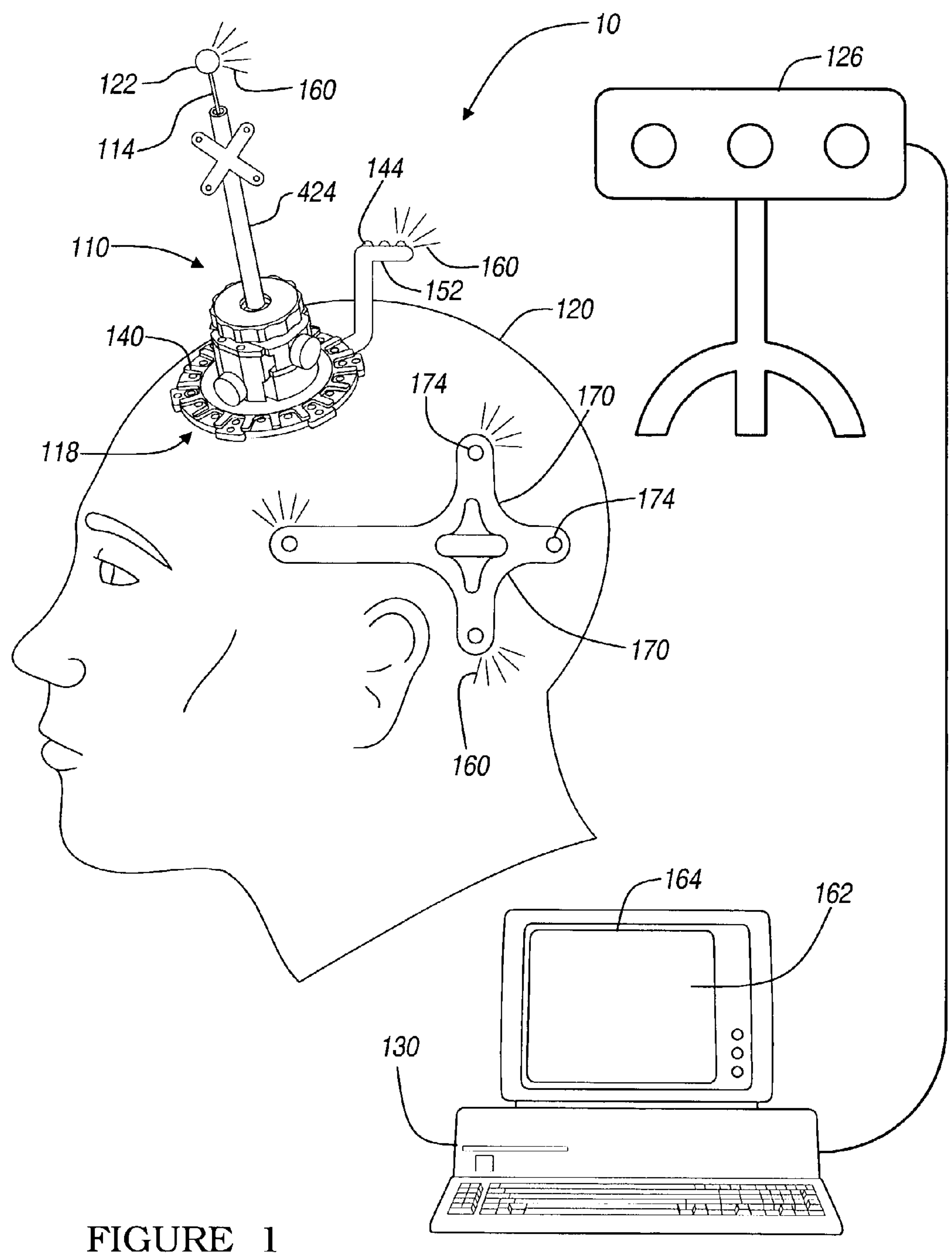
FIG. 1 is a diagram of an image guided system consistent with an embodiment of the present invention.

A description of embodiments of the present invention are described in connection with the accompanying figures. Referring to FIG. 1, an image guided stereotactic surgery system and method consistent with the present invention is illustrated. The system 10 includes an instrument guide unit 110 that is used to guide a surgical instrument 114 during a surgical operation, such as for example an electrode for deep brain stimulation. The instrument guide unit 110 is placed over a burr hole 118 that is cut in the patient's skull 120 to enable operation on the patient's brain. Surgical instrument 114 includes a tracking marker, such as LED 122, that is detected or monitored by a sensor array, such as camera array 126, as described herein. The instrument guide unit 110 may include a mini-reference position frame 152. The mini-reference position frame 152 contains tracking markers, such as LEDs 144, that are also tracked or monitored by the camera array 126. The mini-reference position frame 152 provides a point of reference for locating and imaging the skull. A mini-reference position frame 170 may also be attached to the patient's skull 120 to provide a point of reference for locating and imaging the skull 120. The mini-reference position frame 170 includes LEDs 174. It should be appreciated by those skilled in the art that only one of the mini-reference position frames 152 or 170 is needed to establish reference coordinates for the patient's body, although both may be used.

The manner in which the camera array 126 tracks the positions of a reference frame and a surgical instrument are well known in the art and is therefore only described generally. The camera array 126 includes a plurality of cameras for tracking positions. The cameras can be CCD cameras to detect illumination emitted from the tracking markers. Based on the relative coordinates of the detected markers, the positions of objects can be determined and corresponding representations of the objects can be displayed on the monitor.

The camera array 126 is coupled to a computer system 130 that contains program modules that analyze the signals transmitted from the camera array to determine the relative position of the instrument guide unit, surgical instrument, and relevant body part during a surgical procedure. The computer system 130 also contains an image data set of the body site of interest usually generated by some scanning technique such as CT scanning or MRI. Computer system 130 produces a composite image of the surgical instrument and the image of the area in which a surgeon is operating representing the real time position of the surgical instrument and body part. The composite image varies in accordance with the movement of the patient and surgical instrument. An image guided surgery system suitable for use in connection with the present invention is the STEALTH STATION system available from Sofamor Danek, Inc., located in Memphis, Tenn.

During a surgical operation, the system 10 may include a tracking reference frame 170, which is attached to the patient's skull 120 and contains LEDs 174 that are tracked by the camera array 126. The reference frame 170 may be used as a scanning reference frame during the initial surgical preparations for the patient, with fiducial scanning markers replacing the LEDs 174. It should be understood by those skilled in the art that a separate scanning frame distinct from the reference frame 170 may be used. If distinct scanning and tracking reference frames are used, the frames preferably are the same shape or hold the markers in the same relative positions and mount to the same locations or mounting devices on the body.

Using a preoperative scan such as CT scans, a surgeon identifies a target point in the brain and determines an entry point through the patient's skull. The surgeon plans a surgical trajectory using a computer display of an image 164. The selected target and entry points are stored in a database record for the patient along with the selected surgical trajectory. The orientation of a surgical trajectory line normal to base plate 140 is adjustable within a surgical trajectory cone forming a solid angle of approximately 45 degrees.

After the surgeon attaches the instrument guide unit 110 to the patient's skull, the instrument guide unit 110 is operative to aid in adjusting the x, y, and z coordinates for a surgical instrument as well as the angular trajectory of the instrument. As described in more detail herein and shown in FIG. 4*a*, instrument guide unit 110 includes a base plate 140 to which LEDs 144 may be coupled by means of a mini-reference position frame 152. After attaching instrument guide unit 110, the surgeon can adjust the orientation of the instrument guide unit 110 and the surgical instrument 114. The surgical instrument 114, including an instrument LED 122 fixed relative to the instrument, passes through an opening that extends through the length/depth of the instrument guide unit 110. The z-axis of the surgical instrument is adjusted by advancing or withdrawing the surgical instrument 114 through a guide tube 424. At the same time computer system 130 tracks the depth of instrument 114 by tracking the position of instrument LED 122.

If desired, the position of the instrument, along the z-axis, may be fixed in place by use of a set screw in the tube or other suitable means. Surgical instrument 114 is constrained to follow a fixed trajectory through a central opening through adjusted base plate 140.

Computer system 130 tracks the location and orientation of base plate 140 and the displacement of surgical instrument 114 by tracking markers such as the LEDs in a conventional manner. It should be appreciated that various methods of tracking the position of the surgical instrument may be used. For example, a transducer or magnetic sensing device may be used to track the position of a position indicator attached to the surgical instrument. In the system and method of the present invention, it is important that the LEDs of the reference frame, instrument guide unit, and surgical instrument remain in the visual field of the cameras of the camera array 126 to help produce consistent and accurate locations and representations of objects in the computer system 130. The orientation and distance of the LEDs should be maintained within a range sufficient to ensure accurate and consistent readings. The computer system 130 computes the position of surgical instrument 114 in the coordinate system established during the initial scanning phase. The real time coordinate system can be correlated to the coordinate system established during scanning through use of the reference frame 170 described herein, or other techniques such as those disclosed in U.S. Pat. No. 5,383,454 to Bucholz; U.S. Pat. No. 5,891,034 to Bucholz; U.S. Pat. No. 5,851,183 to Bucholz; and U.S. Pat. No. 5,871,445 to Bucholz. Computer system 130 displays on display monitor 164 a composite image 162 showing the position and orientation of surgical instrument 114 with respect to the patient's head. The surgeon uses the images produced on display 164 to position surgical instrument 114 along the predefined trajectory. When using a system or method consistent with the principals and methods of the present invention, a patient's head does not have to be locked into a stationary position.

Figure 2:
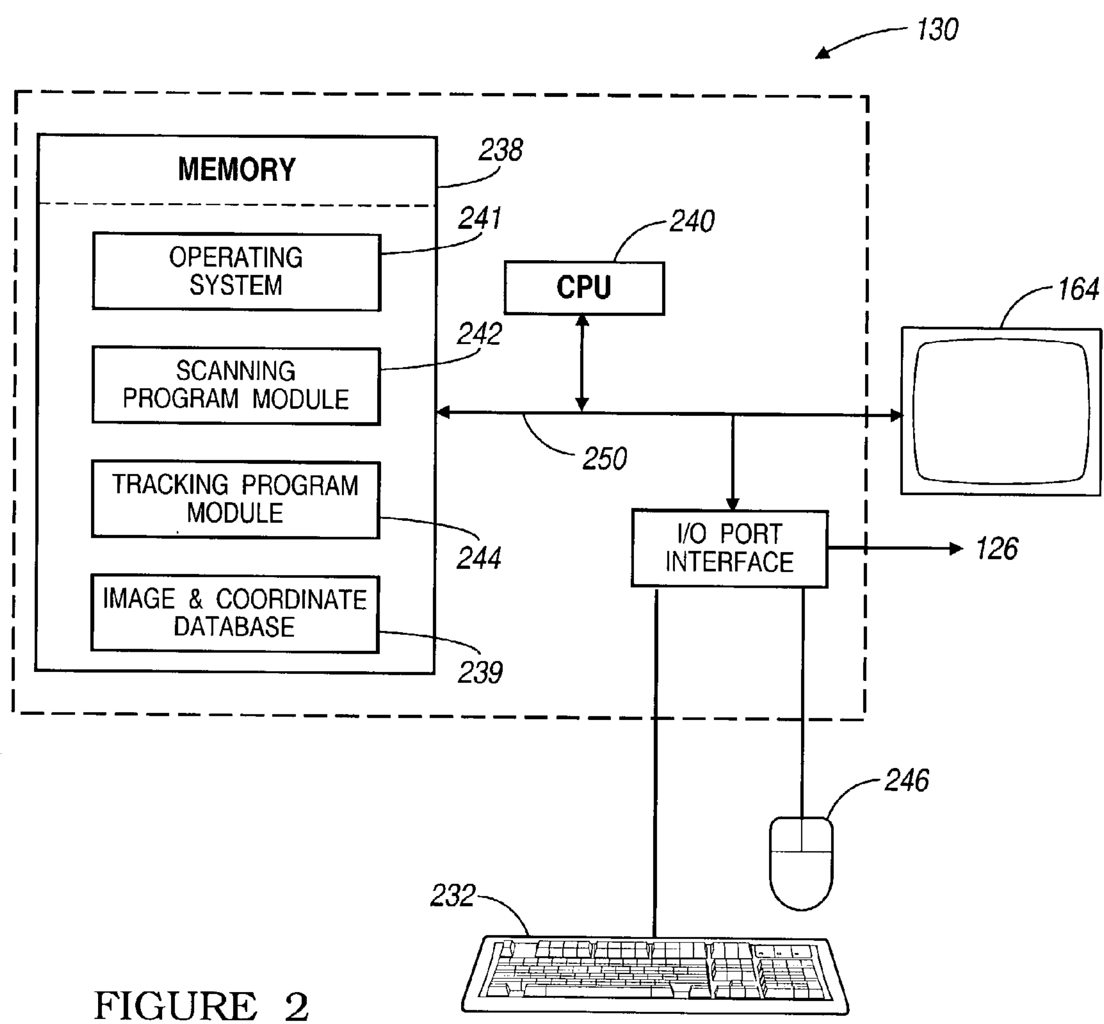
FIG. 2 is a block diagram of a computer system used in connection with the present invention.

Referring to FIG. 2, the general components and modules of a computer system 130 used to perform various processes of the present invention is described. Although a STEALTH STATION image guided system manufactured by Sofamor Danek has been identified, it will be appreciated that the present invention may be utilized in other types of computer systems. One aspect of the computer system includes a graphical user interface system operating in conjunction with a display screen of the display monitor 164. The graphical user interface system is preferably implemented in conjunction with the operating system for displaying and managing the display objects of the system. The graphical user interface system is implemented as part of the computer system 130 to receive input data from a conventional keyboard 232, a mouse 246, a camera array 126 or other input device. For simplicity of the drawings, many components of a standard computer system have not been illustrated such as address buffers, memory buffers and other standard control circuits because these elements are well known and illustrated in the prior art and are not necessary for the understanding of the present invention.

A computer program used to implement the various steps of the present invention is generally located in the memory unit 238, and the processes of the present invention are carried out through the use of a central processing unit (CPU) 240. Those skilled in the art will appreciate that the memory unit 238 is representative of both read-only memory and random access memory. The memory unit also contains a database 239 that stores the data, for example image data, and tables used in conjunction with the present invention. The CPU 240, in combination with computer software, such as an operating system 241, a scanning program module 242, and tracking program module 244, controls the operations and processes of the computer system 130. The processes implemented by the CPU 240 may be communicated as electrical signals along the bus 250 to an input/output device via input output interface 126. The scanning program module 242 performs the processes associated with creating a coordinate reference system and reference images for use in connection with the present invention and as known to those skilled in the art. The tracking program module 244 performs the processes necessary for tracking objects in an image guided system as described herein and as known generally to those skilled in the art.

Figure 3A:
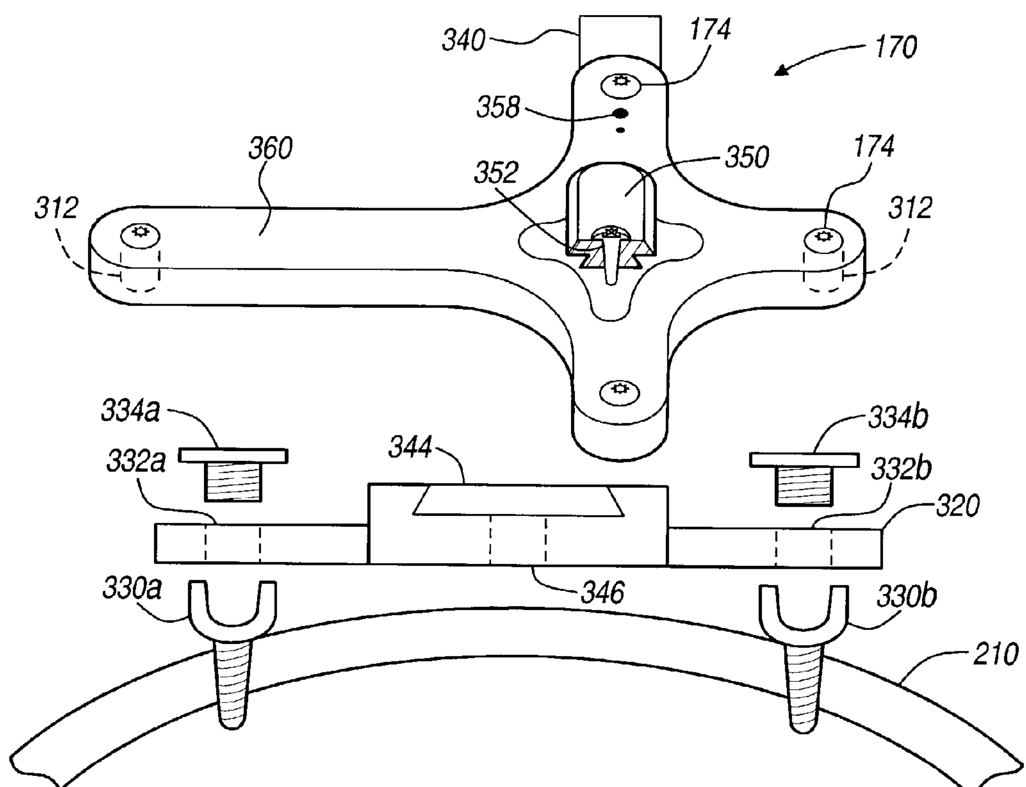
FIG. 3*a* is an exploded view of a reference frame and anchor bar consistent with an embodiment of the present invention.

Referring to FIG. 3*a*, a rigid mini-reference position frame 170 is shown in an exploded view. The mini-reference position frame 170 is made of a material that will not interfere with either the scanning operation or the tracking operation that is to be performed. One material suitable for constructing frame 170 when MRI scans are to be used is polycarbonate. The recesses 312 into which the LEDs 174 or fiducial scanning markers are inserted are preferably "snap-in" recesses that enable the LEDs 174 or fiducial scanning markers to be snapped into place on the mini-reference position frame 170. The design of the mini-reference position frame 170 has a four pronged star shape. The mini-reference position frame 170 has an elongated portion 360 that preferably extends over and to a position in front of the patient's ear (FIG. 1).

Figure 3B:
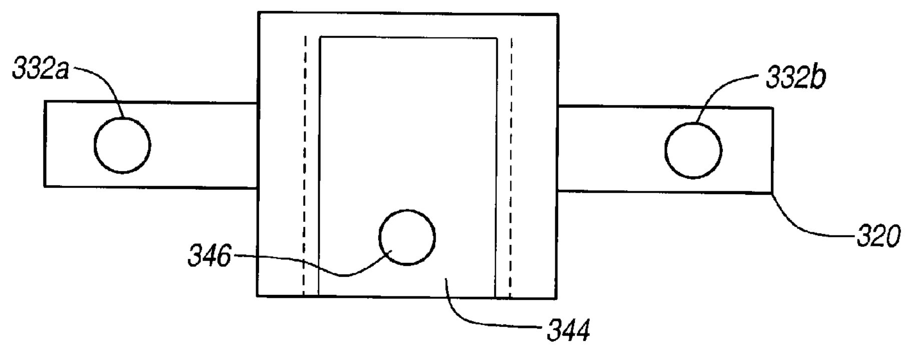
FIG. 3*b* is a top view of an anchor bar used in connection with the present invention.

The mini-reference position frame 170 may be attached to an anchor plate 320 to secure the mini-reference position frame 170 to the skull 120 of the patient. The anchor plate 320 is secured to the skull 120 by securing the anchor plate to anchor screws 330*a* and 330*b* that are screwed into selected locations in the skull 120. The anchor plate 320 has screw holes 332*a* and 332*b* defined therein through which plate screws 334*a* and 334*b* are positioned to screw into the anchor screws 330*a* and 330*b*. The anchor screws 330*a* and 330*b* are preferably located in positions that are directly beneath the axis of the elongated section 360 or that are parallel and in close proximity to the axis. The elongated portion 360 is positioned toward the front of the head and extends above the patient's ear where soft tissue thickness is relatively thin and the skull thickness is near a maximum. The relatively thin tissue thickness enables the anchor screws 330*a* to be implanted easily when local anesthetics are used. Referring also to FIG. 3*b*, a top view of the anchor plate 320 is illustrated.

The mini-reference position frame 170 is illustrated with LEDs 174 secured therein. The LEDs 174 may be screwed, snapped, or otherwise recorded into place as known by those skilled in the art. The mini-reference position frame 170 may also serve as a scanning frame by replacing the LEDs with fiducial scanning makers within the mini-reference position frame 170. The mini-reference scanning frame 170 is attached to the anchor plate 320 by sliding the reference frame slide member 340 into the anchor plate locking cavity 344. The anchor plate locking cavity 344 has a screw hole 346 defined therein for receiving a screw 350 that is inserted through a screw hole 352 of the reference frame slide member 340. The reference frame slide member 340 may be integrally molded as part of the mini-reference position frame 170 or may be secured to the reference frame by welding or by screws 358.

Figure 4A:
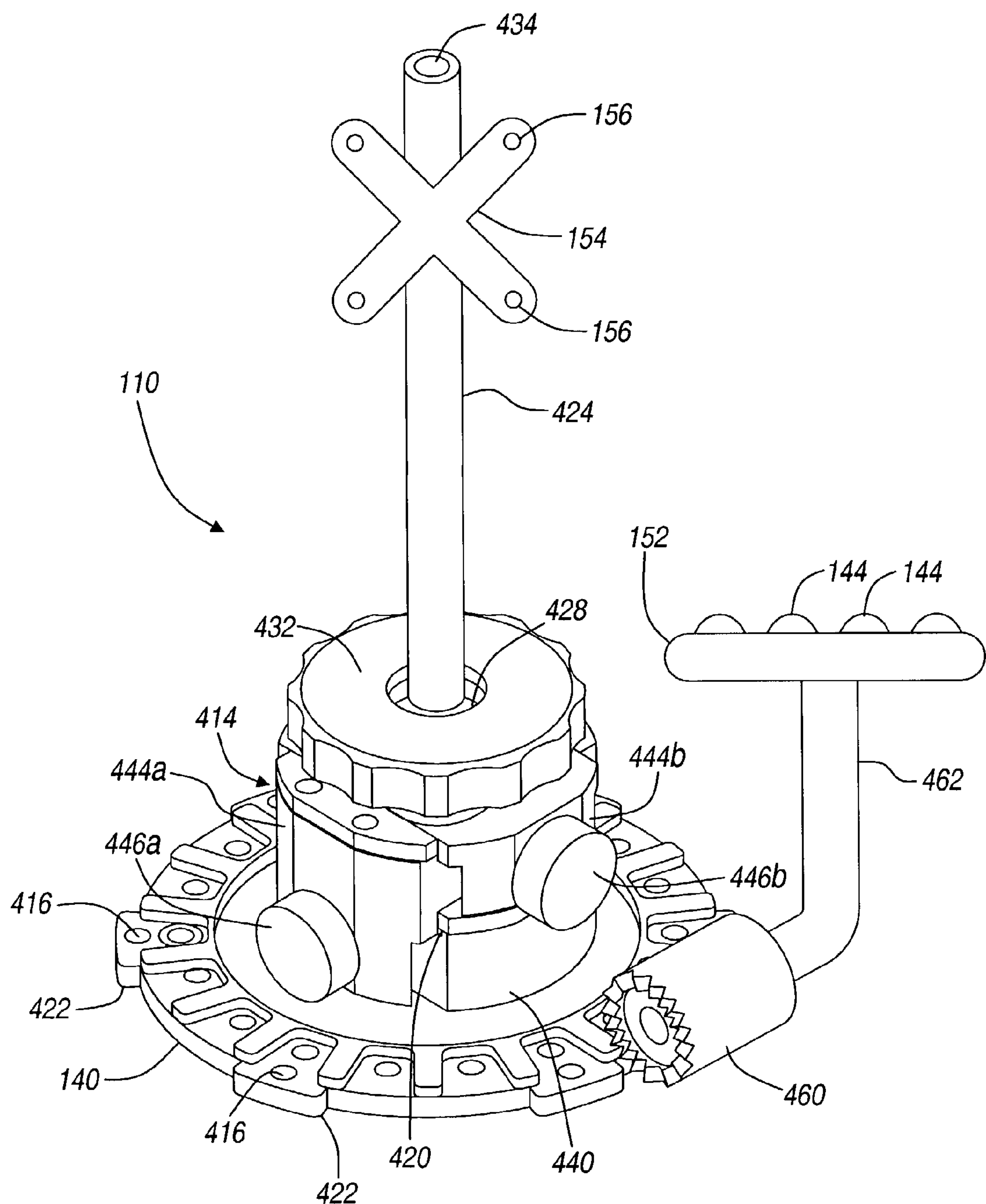
FIG. 4*a* is a view of a base plate and an adjustable base of an instrument guide unit.

Referring to FIG. 4*a*, a description of the instrument guide unit 110 is provided. The instrument guide unit 110, as discussed above, is a stand-alone unit used to aid a surgeon in guiding a surgical instrument to a target point. That is, the instrument guide unit 110 may connect directly to the patient's skull without support from another frame structure.

The instrument guide unit 110 includes an adjustable guidance base 414 coupled to a base plate 140. The base plate 140 may be secured to the skull of a patient by screws that pass through mounting holes 416 of mounting tabs 422.

The instrument guide unit 110 includes a guide tube 424 or upper portion that is used to establish x, y, z and angular coordinates for a surgical instrument during operation on a patient. The guide tube 424 is connected to guide ball 428. The guide ball 428 may pivot within the adjustable guidance base 414 to enable the guide tube 424 to be positioned at selected angles. The guide ball 428 may be moved or translated in x and y directions within the adjustable guidance base 414 to provide x and y adjustable positions for the guide tube 424 attached to the guide ball 428. The movement of the ball in the x and y directions control the x and y coordinates of the trajectory line that a surgical instrument will traverse when operating on a patient. The guide ball 428 is secured within the adjustable guidance base 414 by a locking plate 432. The locking plate 432 may be rotated into a locking position to lock the guide ball 428 into a fixed position to maintain a selected trajectory. The locking plate 432 locks the guide ball 428, and consequently the guide tube 424, in place when the locking plate 432 is screwed firmly down onto the ball. When the locking plate 432 is screwed firmly down onto the ball 428, the ball 428 is clamped into a stationary position within the adjustable guidance base 414. A surgical instrument 114 (FIG. 1), including an instrument LED 122 (FIG. 1), is free to pass through a central opening 434 of the guide tube 424. By locking the guide ball 428 in a selected position, the surgical instrument 114 is constrained to follow the fixed trajectory through an opening of the base plate 140.

The adjustable guidance base 414 includes several components. These components include a guidance mounting base 440, an x-direction translation base 444*a* and a y-direction translation base 444*b*. The translation bases 444*a* and 444*b* are adjustable in an x and y direction relative to the base plate 140. The translation bases 444*a* and 444*b* include adjustable translation knobs 446*a* and 446*b*, respectively. The adjustable translation knobs 446*a* and 446*b* enable the x-direction translation base 444*a* and y-direction translation base 444*b* to be adjusted in the x and y directions, respectively. Thus, the adjustable guidance base 414 is adjustable in the x and y directions to control the x and y position of the guide ball 428 and guide tube 424. The combination of an x and y translation bases form an x and y translation table for setting the x and y coordinate locations of the guide ball 428. By turning the adjustable translation knobs 446*a* and 446*b* in a clockwise or counter-clockwise direction, the guide ball 428 moves in the corresponding direction, along the axis of the adjustable translation knob.

As generally discussed above, the camera array 130 tracks or determines the position of objects, such as a surgical instrument, surgical structure or body part, by identifying reference points established on the objects. Particularly, the position of LEDs are tracked as reference points for objects being monitored by a system or method operating according to the present invention. The position of relevant objects may be tracked by attaching a mini-reference position frame to the object. A mini-reference position frame 154 may be permanently attached or removably attached to a selected object, such as the guide tube 424. The mini-reference position frame 154 includes a plurality of LEDs 156 that may be tracked by the camera array described above. By detecting the locations of the LEDs 156 on the mini-reference position frame 154, the computer system may track the position of the guide tube 424 for calculating coordinates of the guide tube 424 according to the present invention. The mini-reference position frame 154 may be attached to the guide tube 424 by suitable clamping means as known by those skilled in the art.

In addition to tracking the position of the guide tube 424, the position of the base plate 140 may also be tracked. The position of the base plate 140 is tracked by determining the position of a mini-reference position frame 152. The mini-reference position frame 152 has LEDs 144 positioned thereon that serve as coordinate reference points that are tracked by the computer system via the camera array 130 (FIG. 1). The mini-reference position frame 152 is attached to the base plate 140 in a fixed relationship. The mini-reference position frame 152 may be connected to base plate 140 through starburst connector 460. Starburst connector 460 may be removably or fixedly attached to the base plate 140. Starburst connector 460 has an opening to fixedly receive an extension arm 462 that supports mini-reference position frame 170. The minireference position frame 152, which is mounted in a stationary position relative to the patient's head throughout the surgical procedure, provides a reference point for base plate 140. The minireference position frame 152 thereby provides a reference location for the burr hole in the patient's skull and allows the position of the burr hole and the patient's skull to be continuously tracked by the computer station.

Alternatively, a tracking reference frame, such as tracking reference frame 170, may be used to track the location of the body part. In that case, the position of reference frame 170 affixed to the patient's skull may be registered with respect to the burr hole by placing a registration probe having an LED or other tracking element at the site of the burr hole. The computer system can then determine the position of tracking reference frame 170 with respect to the burr in the patient's skull.

During a surgical procedure, a surgical instrument 114 is passed through a central opening of base plate 140 into the brain or other area of interest. Adjusting the angle of the guide tube 424 adjusts the trajectory of the guide tube 424 and the instrument passing through the guide tube. Adjusting the orientation of adjustable guide base 414 adjusts the x and/or y position of the guide tube and consequently the trajectory of the guide tube. Moving the surgical instrument up or down within the guide tube 424 adjusts the z-position of the surgical instrument. In all orientations, the trajectory passes through a single point on the central axis of base plate 140 near the surface of the skull.

Figure 4C:
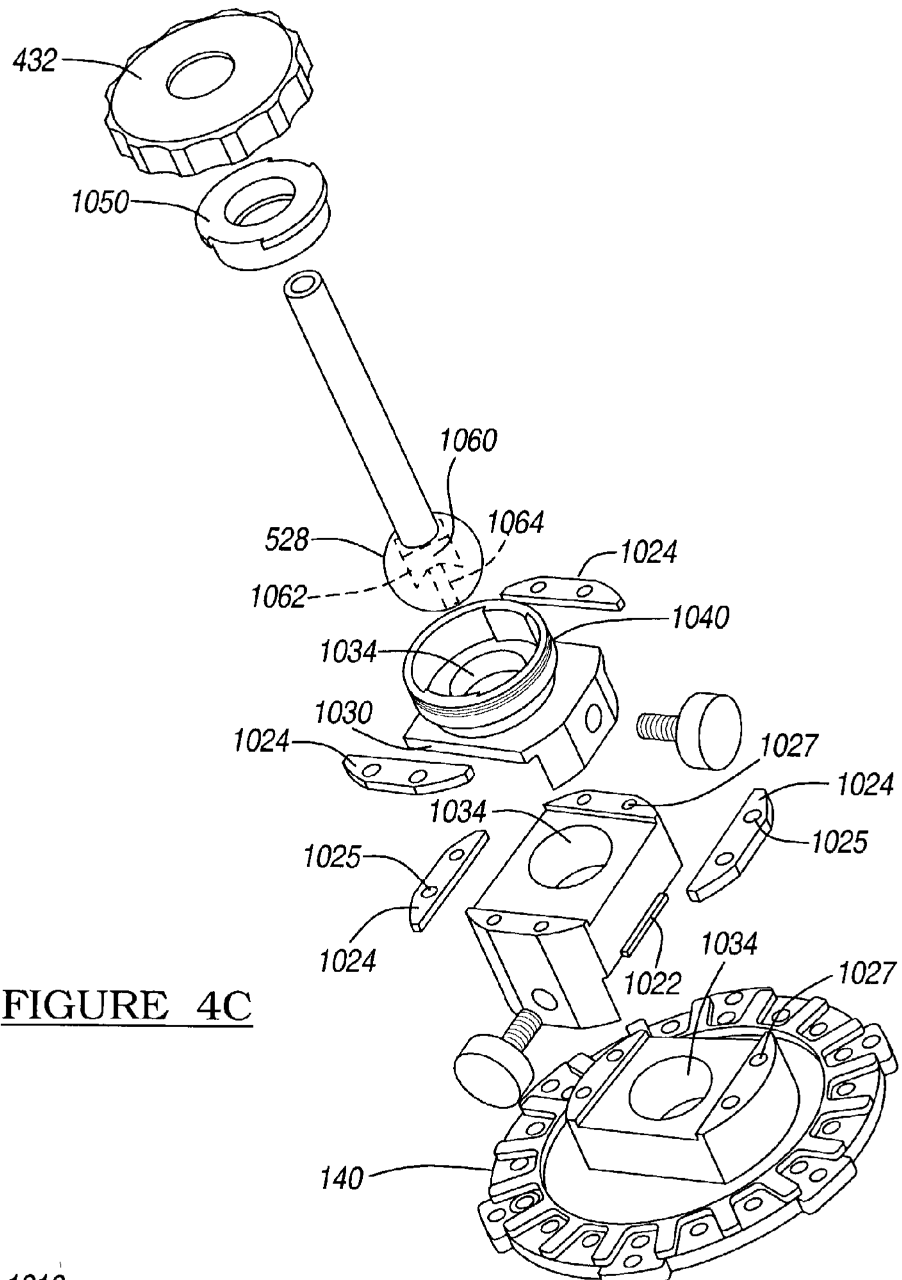
FIG. 4*c* is an exploded view of the adjustable base of an instrument guide unit.
Figure 4B:
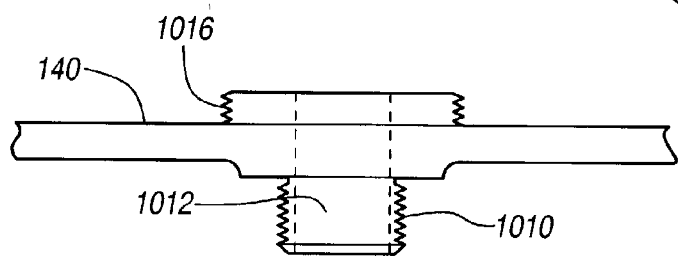
FIG. 4*b* is a side view of the base plate.

Referring to FIG. 4*b*, a side view of the base plate 140 is illustrated. As shown in FIG. 4*b*, the base plate 140 has a lower screw portion 1010 coupled to the lower side of the base plate 140. The lower screw portion 1010 has an opening 1012 defined therein that extends up through the base plate 140 and through an upper screw portion 1016. The upper screw portion 1016 provides a mounting thread for the guidance mounting base 440. The guidance mounting base 440 is firmly secured to the base plate 140 by screwing the guidance mounting base 440 on to the upper screw portion 1016. The mounting base 440 is stationary relative to the base plate 140 and has an opening 1034 defined therein through which a surgical instrument may pass.

Referring to FIG. 4*a* and FIG. 4*c* (an exploded view of the instrument guide unit 110), mounting base 440 provides a mechanism for attaching and locking into place the x-direction translation base 444*a* to the mounting base. The mounting base 440 has x-translation base mounting channels 420 that receives x-direction translation base mounting extensions 1022 (FIG. 4*c*) that extend from the x-translation base 444*a*. The x-translation base mounting channel 420 is formed when a channel top piece 1024 (FIG. 4*c*) is secured to the mounting base 114 by screws positioned through screw holes 1025 and 1027 (FIG. 4*c*). The x-translation base mounting extensions 1022 which extend from the x-direction translation base 444*a* slide into the x-base mounting channel 1020 for coupling to the guidance mounting base 440.

Translation base 444*a* also has a y-translation base mounting channel 1026 for mounting the y-direction translation base 444*b* to the x-direction translation base 444*a*. The y-direction translation base 444*b* has a y-translation base channel mating extension 1030 that extends therefrom. The y-translation base channel mating extension 1030 is designed to slide into the y-translation base mounting channel 1026 to provide a snug fit for the extension 1030. The extensions 1022 and 1030 may slide back and forth in the respective channels when the corresponding translation knob 446 is turned or screwed in or out. It should be appreciated that each of the base members has an opening 1034 defined therein to allow the surgical instrument to pass from the guide tube and down through the opening 1012 of the base plate 140.

The y-direction translation base 744*b* includes a locking plate screw portion 1040 onto which the locking plate 432 is screwed. However, before the locking plate 732 is screwed onto the locking plate screw portion 1040, the guide tube 424 and guide ball 428 are positioned into a guide pivot member located between the bases 444*a* and 444*b*. The opening of the locking plate 432 is positioned over the guide tube 434. The mini-reference position frame 152 is then coupled to the guide tube 424 as illustrated in FIG. 4*a*.

The guide ball 428 has an opening 1060 defined therein. The opening 1060 narrows in diameter from the upper portion to the lower portion of the guide ball 428. Particularly, the opening 1060 has a wide diameter shelf 1062 that is slightly larger than the diameter of the guide tube 424 to enable the guide tube 424 to be positioned on the shelf 1062. A lower portion 1064 of the opening 1060 has a diameter that is more narrow than the diameter of the guide tube 424.

The narrow diameter of the lower portion 1064 of the opening 1060 prevents the guide tube 424 from sliding entirely through the opening 1060 of guide ball 428 and enables the surgical instrument to pass through.

In use, the mounting base 440, translation bases 444*a* and 444*b*, guide tube 424 with guide ball 428 and locking plate 432 assemblies are assembled as a unit prior to the beginning of the surgical procedure. The base plate 140, however, is not typically assembled as part of the instrument guide unit 110 prior to surgery. The base plate 140 is preferably mounted to the patient's skull without the adjustable guidance base 414 attached. The base plate 140 is secured to the skull over the burr hole in the patient's skull using three or more bone screws that pass through mounting holes 416 through mounting tabs 422. By not attaching the mounting and translation portions of the instrument guide unit 110 to the base plate 140 prior to the base plate being screwed into the patient's skull, the surgeon can more precisely and easily screw in the base plate 140 to the patient's 's skull at the selected location.

Figure 5D:
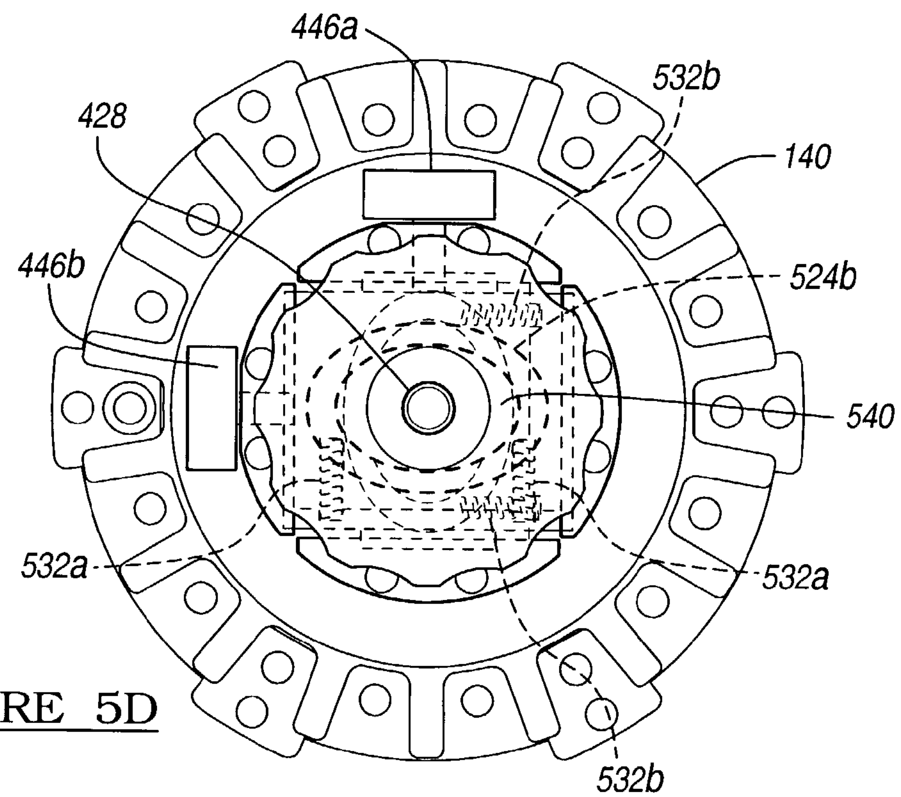
FIG. 5*d* is a top view of the adjustable guidance base taken along line 5*d*—5*d* of FIG. 5*a;*
Figure 5A:
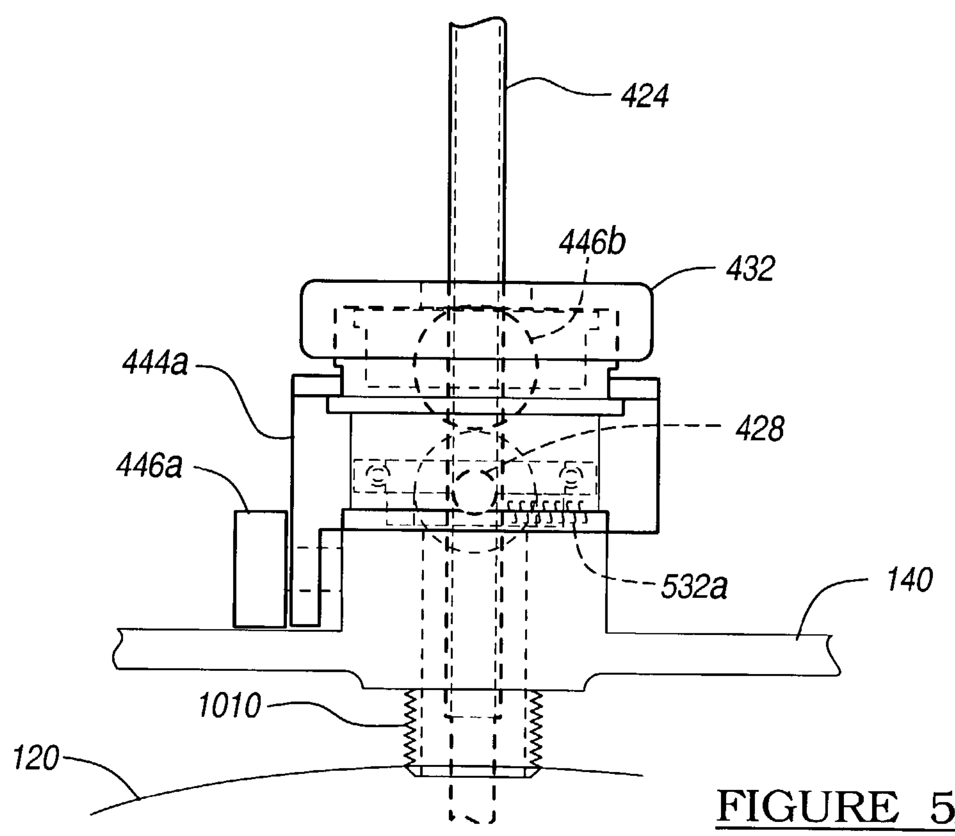
FIG. 5*a* is a side view of the instrument guide unit showing components that move a guide tube in the x and y direction.
Figure 5B:
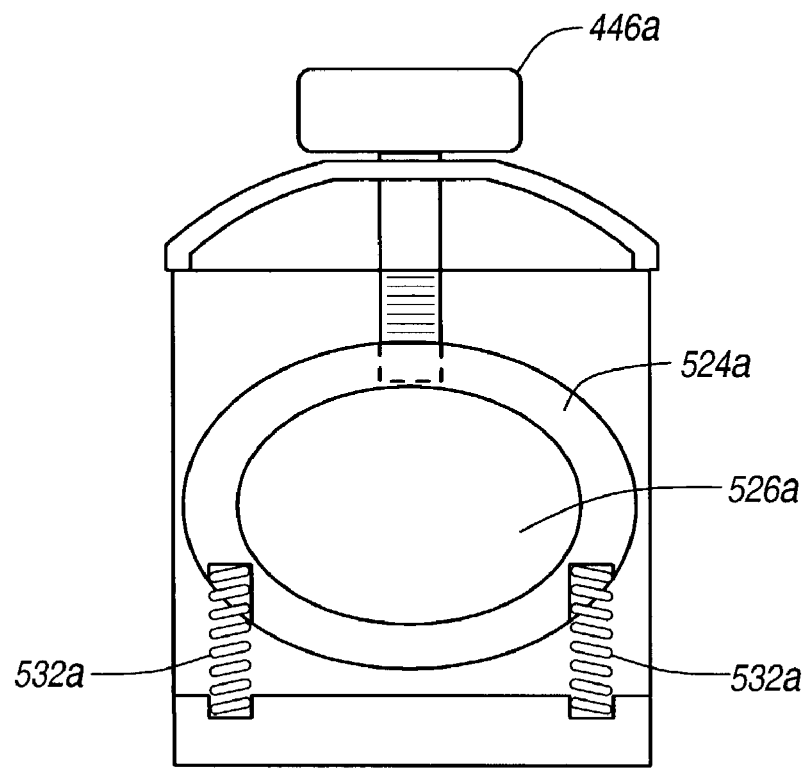
FIG. 5*b* is a top view of the x translation base components.

Referring to FIG. 5*a*, a side view of the instrument guide unit 110, as attached to a patient's skull, is illustrated. In FIG. 5*a*, the mechanisms used to control movement of the guide tube 424 and guide ball 428 in the x and y directions are illustrated. FIG. 5*a* illustrates a side view of the instrument guide unit 1 10 with the component parts of the x and y translation table shown by the hidden on dashed lines. The guide ball 428 is moved in the x direction when the translation knob 446*a* is rotated. When the translation knob 446*a* is rotated, the screw portion 1120 of the translation knob 446*a* rotates within an oval shaped guide ring 524*a*. The manner in which the translation knob and guide ring operate to move in the x direction is illustrated in FIG. 5*b*. FIG. 5*b* is a top view of the x translation base 444*a* components.

When the translation knob is rotated, the guide ring 524*a* is either pulled toward the side of the translation base on which the knob is located or it is pushed away from the side of the translation base on which the knob is located. A portion of the guide ball 428 rests within the opening 526*a* of the guide ring 524*a*. Thus, when the guide ring 524*a* is moved by rotation of the translation knob 446*a*, the guide ball moves in the fixed direction that corresponds to the direction of rotation of the translation knob 446*a*. Springs 532*a* are attached to the guide ring 524*a* on each side of the opening 526*a* defined in the guide ring. The springs 532*a* are attached to the wall of the translation base 444*a* that is opposite of the wall of the translation base 444*a* on which the translation knob 446*a* is located. The springs 532*a* help to reduce backlash or stabilize the guide ring when the guide ring is moved.

Figure 5C:
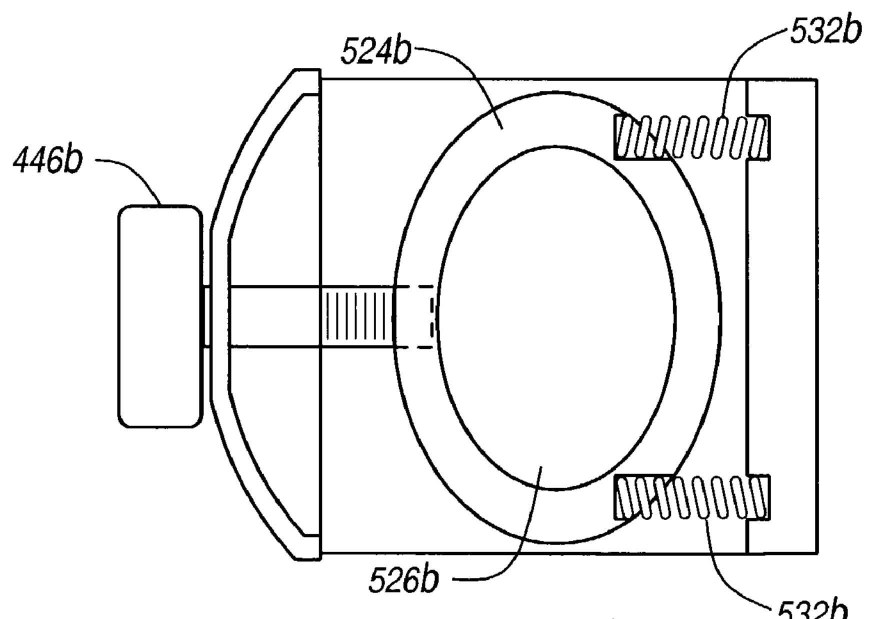
FIG. 5*c* is a top view of the y translation base components.

Referring to FIG. 5*c*, a top view of the y translation base including its y direction translation components is illustrated. The operation of the guide ring 524*b* and translation knob 726*b* and springs 532*b* operate in the same manner as the components discussed in connection with FIG. 5*b* except that the direction of movement is in the y direction.

The oval shape of the opening 526*a* and 526*b* of the guide rings 524*a* and 526*b* enable the movement of the guide ball 428 in the desired direction. Referring to FIG. 5*d*, the guide ball 528 fits firmly against the walls of the opening 526*b* that are perpendicular to the direction in which the translation knob 446*b* moves. However, spaces 540 are defined between the spherical guide ball 428 and the oval shape sides of the walls of the opening 526*a* that are perpendicular to the x direction of movement. Thus, when the translation knob 446*a* is rotated within the translation base 444*a*, the guide ball 428 is free to move in the x direction in the spaces 540 illustrated. It should be appreciated that spaces similar to the spaces 540 are defined between the guide ball and each guide ring 524*b* in the corresponding direction.

Figure 6:
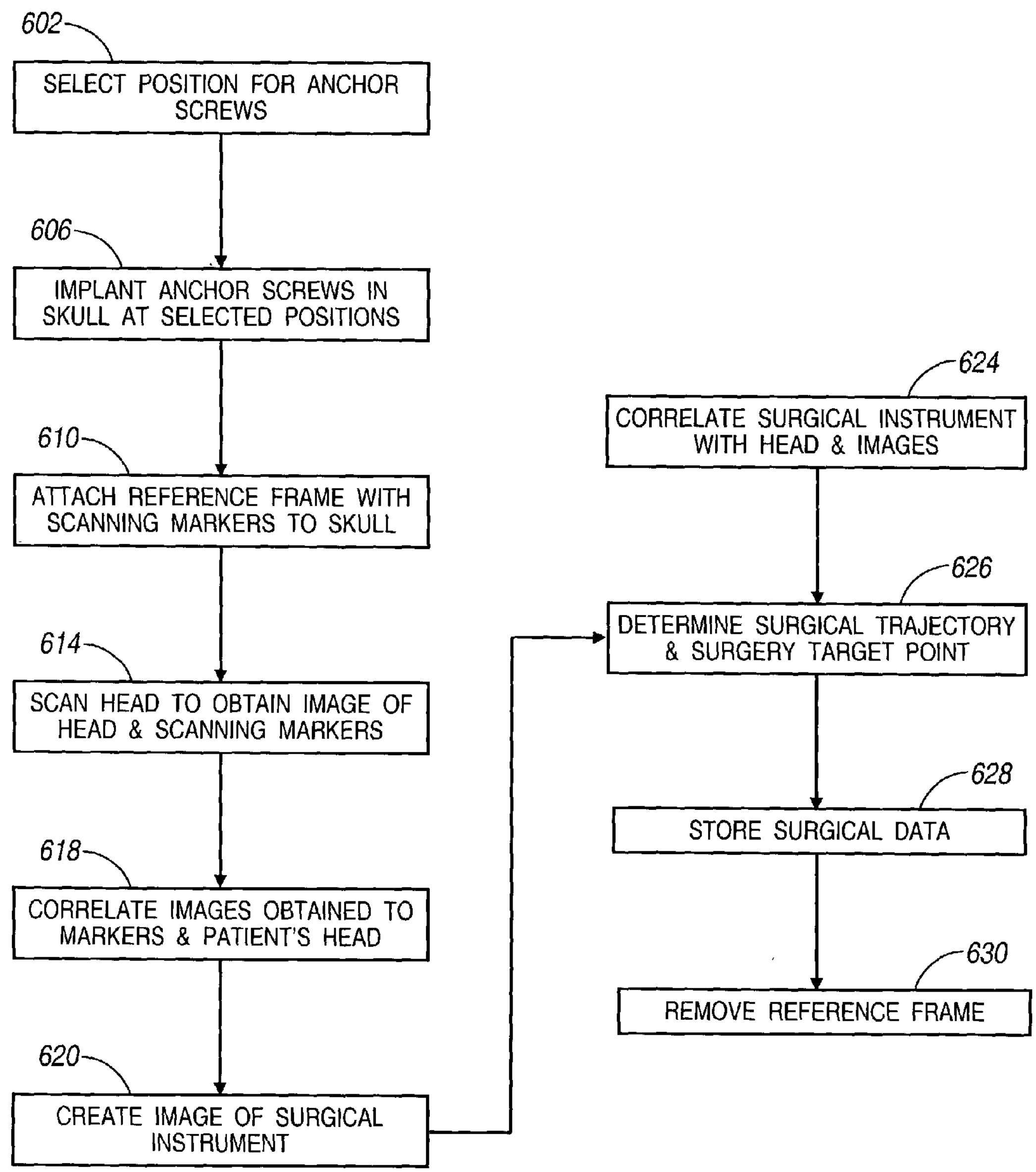
FIG. 6 is a flow diagram of scanning phase processes associated with image guided surgery.

Referring to FIG. 6, the processes or steps associated with pre-surgery procedure is illustrated. To begin, a surgeon selects (step 602) a position for anchor screws to be inserted into a patient's skull for securing a reference frame to the patient's skull. The anchor screws are implanted in the patient's skull (step 606) at the selected positions. A reference frame, with fiducial scanning markers, is attached to the person's skull using the implanted anchor screws. The patient's head is then scanned (614) to obtain an image of the head and the fiducial scanning markers placed on the patient's body. After scanned images have been obtained, the images are correlated (618) with the scanning markers located on that patient's body or head to provide an appropriate registration or coordinate frame of reference for use in the tracking stage of surgery. An image of the surgical instrument is created (620) for use during the tracking stage. The image of the surgical instrument is correlated with various positions on the head, such as at the fiducial scanning markers, so that the computer system can provide accurate depictions of the location of the surgical instrument with respect to the head or body during a surgical procedure. A surgeon determines (step 626) the surgical trajectory that the surgeon will take to reach the target point of the surgery.

As known to those skilled in the art, the manner in which a surgical trajectory is determined is known in the image guided surgery art and is not discussed in detail herein. After the surgeon determines the surgical trajectory, all information regarding the coordinate reference points, images, and surgical trajectory are stored to the memory of the computer system and the database for the specific patient (step 628). If desired, the surgeon may remove the reference frame (step 630) from the patient's head.

Figure 7:
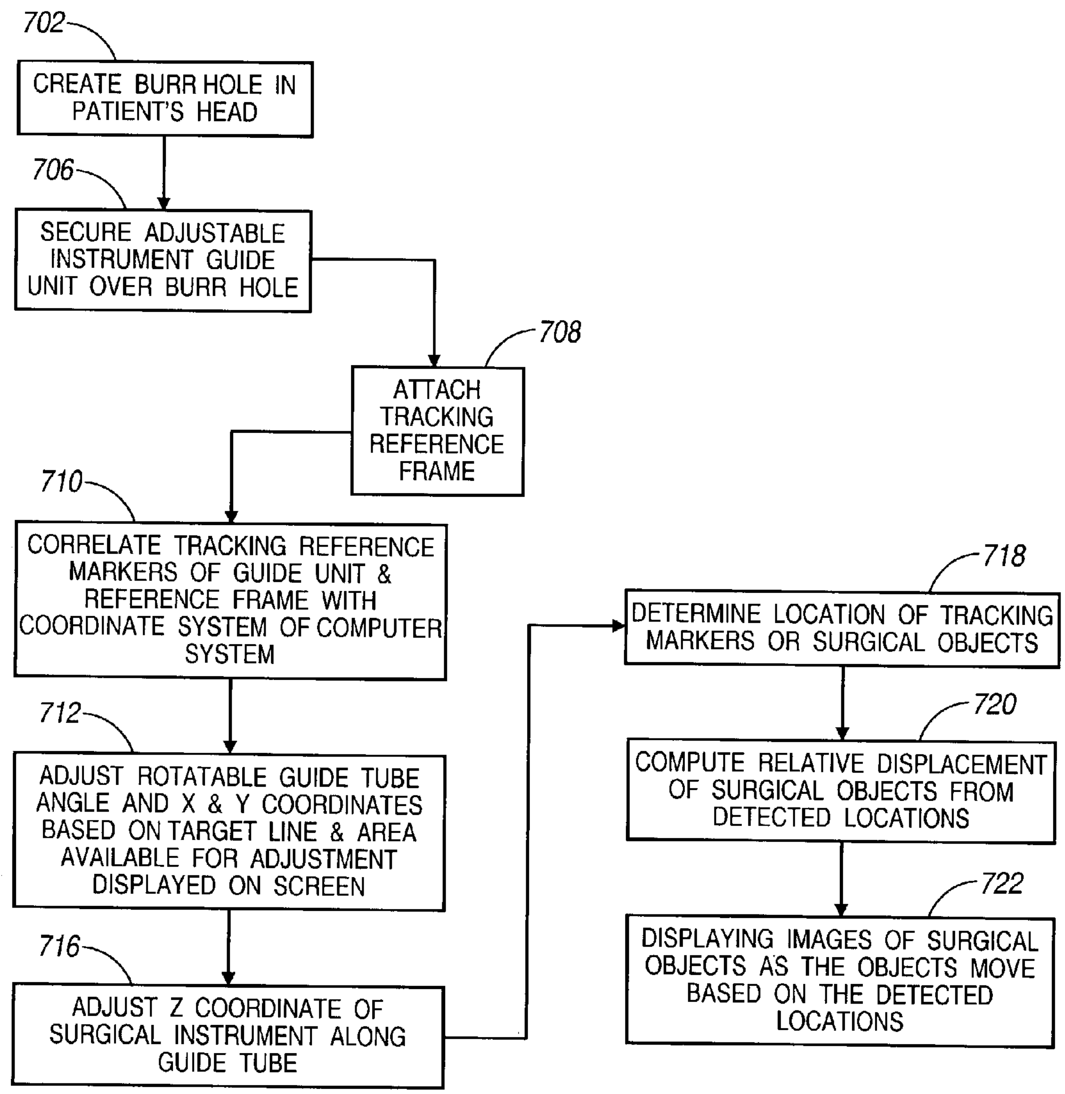
FIG. 7 is a flow diagram of processes associated with the tracking phase of an image guided surgical procedure.

Referring to FIG. 7, the processes or steps associated with the tracking or surgical phase is discussed. A surgeon creates a burr hole (step 702) in the patient's head. After the burr hole has been created in the patient's head, the surgeon secures (step 706) the adjustable instrument guide unit within the burr hole by screwing the lower screw member of the adjustable guide unit into the patient's head. The surgeon also attaches the tracking reference frame (step 708) to the patient's skull for accurately tracking movements of the patient's head.

After the various markers have been positioned on a patient's head, the computer system correlates the tracking reference markers with the coordinate system of the computer system (step 710). The angle and x and y coordinates of the guide tube may be adjusted based on the target line determined by the surgeon and the defined area for which adjustment of the guide tube may occur (step 712). As a surgeon adjusts the guide tube, image information reflecting the change is displayed on the display screen. The surgeon may adjust the z-coordinate of the surgical instrument by moving the surgical instrument up and down the guide tube (step 716). During the tracking phase, the computer system continuously determines the location of tracking markers from surgical objects (step 718). The computer system also computes (step 720) the relative displacement of the surgical object being tracked from the detected locations. The images of the surgical objects are displayed as the objects are moved during a surgical procedure (step 722). The images are displayed based upon the locations detected for the tracking markers.

While this invention has been described in connection with LEDs and a camera array, it should be recognized that other tracker elements and sensor arrays known in the art could be used, such as for example sonic, optic, or electromagnetic, as well as optical reflectors and a corresponding camera system. It should be appreciated that many modifications and adaptations can be made to the embodiments described herein without departing from the scope of the appended claims.

What is claimed is:

1. An image guided surgery system for use in image guided surgery, comprising:

- an instrument guide unit operable to guide a surgical instrument into a body of a patient, said instrument guide unit including,
- an instrument guide operable to guide a surgical instrument into the body of the patient, said instrument guide including a first set of tracking elements,
- a base unit operable to be secured to the body in an area in which surgery is to occur, said base unit being coupled to said instrument guide and having a second set of tracking elements, and
- an adjustment mechanism operably connecting said base unit and said instrument guide as a unit that is operable to adjust said instrument guide relative to said base unit;
- a tracking device operable to track said first set of tracking elements associated with said instrument guide and said second set of tracking elements associated with said base unit;
- a computer system operable to determine a location of said base unit and an orientation of said instrument guide by use of said first and second sets of tracking elements; and
- a display operable to display representations of the area in which surgery is to occur and a trajectory line defined by an orientation of said instrument guide relative to said base unit.

2. The image guided surgery system of claim 1 wherein said adjustment mechanism is operable to adjust said instrument guide in lateral directions with respect to a surface of said area.

3. The image guided surgery system of claim 2 wherein said instrument guide includes a guide tube and a guide ball coupled to said guide tube.

4. The image guided surgery system of claim 3 wherein said adjustment mechanism is operable to adjust said guide ball in lateral directions with respect to said base unit and enable said guide ball to be rotated in angular positions, wherein lateral and angular positions of said guide tube is adjusted at said guide ball.

5. The image guided surgery system of claim 1 wherein said second set of tracking elements associated with said base unit are used as a reference frame.

6. The instrument guide of claim 1 wherein said first set of tracking elements and said second set of tracking elements are selected from a group comprising optical, sonic, electromagnetic, optical reflectors, LEDs, camera array, transducers, magnetic and a combination thereof.

7. The image guided surgery system of claim 1 further comprising said surgical instwment and a third tracking element associated with said surgical instrument, wherein a depth of said surgical instrument may be determined.

8. The image guided surgery system of claim 7 wherein said surgical instrument is an electrode.

9. An image guided surgery system for use in image guided surgery, comprising:

- an instrument guide operable to guide a surgical instrument into a body of a patient;
- a first tracking element connected directly to said instrument guide; and
- a base unit operable to be fixedly connected to the body in an area in which surgery is to occur, said base unit being coupled to said instrument guide, wherein a location of said instrument guide may be determined by use of said first tracking element associated with said instrument guide.

10. The image guided surgery system of claim 9 further comprising said surgical instrument having a second tracking element associated with said surgical instrument, wherein a location of said surgical instrument may be determined by use of said second tracking element associated with said surgical instrument.

11. The image guided surgery system of claim 10 further comprising a third tracking element associated with said base unit, wherein a location of said base unit may determine the use of said third tracking element associated with said base unit.

12. The image guided surgery system of claim 10 wherein said surgical instrument is an electrode.

13. The image guided surgery system as defined in claim 11 wherein said third tracking element is used as a fiducial marker.

14. The image guided surgery system of claim 11 wherein said first tracking element, said second tracking element, and said third tracking element is selected from a group comprising optical, sonic, electromagnetic, optical reflectors, LEDs, camera array, transducers, magnetic and a combination thereof.

15. The image guided surgery system of claim 10 wherein said second tracking element is a transducer coupled to said surgical instrument.

16. The image guided surgery system of claim 15 wherein said transducer is an optical transducer.

17. The image guided surgery system of claim 15 wherein said transducer is a magnetic transducer.

18. The image guided surgery system of claim 11 wherein said location of said instrument guide is an orientation of said instrument guide, said location of said surgical instrument is a depth of said surgical instrument, and said location of said base unit is an X and Y position of said base unit.

19. The image guided surgery system of claim 11 wherein said first tracking element includes a plurality of first tracking elements and wherein said third tracking element includes a plurality of third tracking elements.

20. The image guided surgery system for use in image guided surgery, comprising:

a surgical instrument operable to be used in image guided surgery;

a first tracking element associated with said surgical instrument;

an instrument guide operable to guide said surgical instrument into a body of a patient; and a base unit sized and operable to be secured to and substantially only carried on the body in an area in which surgery is to occur, said base unit being coupled to said instrument guide, wherein a location of said surgical instrument may determined by use of said first tracking element associated with said surgical instrument.

21. The image guided surgery system of claim 20 further comprising a second tracking element associated with said instrument guide, wherein the location of said instrument guide may be determined by use of said second tracking element associated with said instrument guide.

22. The image guided surgery system of claim 20 further comprising a second tracking element associated with said base unit, wherein the location of said base unit may be determined by use of said second tracking element associated with said base unit.

23. The image guided surgery system of claim 21 wherein said second tracking element includes a plurality of second tracking elements associated with said instrument guide and operable to be used to determine the orientation of said instrument guide.

24. The image guided surgery system of claim 22 wherein said second tracking element associated with said base unit includes a plurality of second tracking elements associated with said base unit and operable to be used to determine an X and Y position of said base unit.

25. An image guided surgery system for use in image guided surgery, comprising:

an instrument guide operable, to guide a surgical instrument into a body of a patient;

a base unit operable to be connected to the body in an area in which surgery is to occur, said base unit being coupled to said instrument guide;

a first tracking element associated with said base unit, wherein a location of said base unit may be determined by use of said first tracking element associated with said base unit; and a second tracking element associated with said instrument guide, wherein a location of said instrument guide may be determined by use of said second tracking element associated with said instrument guide.

26. The image guided surgery system of claim 25 further comprising said surgical instrument having a second tracking element associated with said surgical instrument, wherein a location of said surgical instrument may be determined by use of said second tracking element associated with said surgical instrument.

27. The image guided surgery system of claim 25 wherein said first tracking element includes a plurality of first tracking elements associated with said base unit and said second tracking element includes a second plurality of tracking elements associated with said instrument guide.

28. The image guided surgery system of claim 25 wherein said first tracking element is used as a fiducial marker.

29. The image guided surgery system of claim 25 wherein the location of said base unit includes an X and Y position of said base unit, wherein a location of said instrument guide includes an orientation of said instrument guide.

30. The image guided surgery system of claim 26 wherein the location of said base unit includes an X and Y position of said base unit, wherein a location of said surgical instrument is a depth of said surgical instrument.

31. The image guided surgery system for use in image guided surgery, comprising:

a surgical instrument operable to be used in image guided surgery;

a first tracking element associated with said surgical instrument;

an instrument guide operable to guide said surgical instrument into a body of a patient; and a base unit operable to be secured to the body in an area in which surgery is to occur, said base unit being coupled to said instrument guide, wherein a location of said surgical instrument may determined by use of said first tracking element associated with said surgical instrument; and a second tracking element associated with said base unit;

wherein a location of said base unit is determined by use of said second tracking element associated with said base unit.

32. The system of claim 31, wherein at least one of said first tracking element, said second tracking element, or combinations thereof are fiducial markers operable to be used to register an image to a patient.

* * * * *